United States Patent [19]

Mundy et al.

[11] Patent Number: 5,914,233
[45] Date of Patent: Jun. 22, 1999

[54] SCREENING ASSAY FOR THE IDENTIFICATION OF AGENTS WHICH ALTER EXPRESSION OF PTH-RP

[75] Inventors: Gregory R. Mundy; Wolfgang E. Gallwitz, both of San Antonio, Tex.

[73] Assignee: Osteo Screen, San Antonio, Tex.

[21] Appl. No.: 08/915,868

[22] Filed: Aug. 21, 1997

Related U.S. Application Data

[60] Provisional application No. 60/025,215, Aug. 23, 1996.
[51] Int. Cl.$^6$ .......................... C12Q 1/68; G01N 33/566; C12N 5/10
[52] U.S. Cl. .............................. 435/6; 435/7.1; 435/7.21; 435/7.23; 435/69.1; 435/29; 435/375; 436/501
[58] Field of Search ............................. 435/6, 7.1, 7.2, 435/7.21, 7.23, 69.1, 29, 375; 436/501

[56] References Cited

FOREIGN PATENT DOCUMENTS

| | | |
|---|---|---|
| 0487298 | 5/1992 | European Pat. Off. . |
| WO 96/22790 | 8/1996 | WIPO . |

OTHER PUBLICATIONS

Bouizar Z, Spyratos F, Deytieux S, de Vernejoul MC, Jullienne A. Polymerase chain reaction analysis of parathyroid hormone–related protein. *Cancer Res* 53: 5076–5078, 1993.

Bundred NJ, Walker RA, Ratcliffe WA, Warwick J, Morrison JM, Ratcliffe JG. Parathyroid hormone related protein and skeletal morbidity in breast cancer. *Eur J Cancer* 28: 690–692, 1992.

Burtis WJ, Wu T, Bunch C, Wysolmerski JJ, Insogna KL, Weir EC, Broadus AE, Stewart AF. Identification of novel 17,000 dalton parathyroid hormone–like adenylate cyclase–stimulating protein from a tumor associated with humoral hypercalcemia of malignancy. *J Biol Chem* 262: 7151–7156, 1987.

Guise TA, Yoneda T, Yates AJ, Mundy GR. The combined effect of tumor–produced parathyroid hormone–related protein and transforming growth factor α enhance hypercalcemia in vivo and bone resorption. *J Clin Endocrinol. Metab.* 77:40–45, 1993.

Karaplis AC, Luz A, Glowacki J, Bronson RT, Tybulewicz VL, Kronenberg HM, Mulligan RC. Lethal skeletal dysplasia from targeted disruption of the parathyroid hormone–related peptide gene. *Genes Dev* 8:277–289, 1994.

Lanske B, Karaplis AC, Lee K, Luz A, Vortkamp A, Pirro A, Karperien M, Defize LHK, Ho C, Mulligan RC, Abou–Samra A, Juppner H, Segre GV, Kronenberg HM. PTH/PTHrP receptor in early development and indian hedgehog–regulated bone growth. *Science* 273:663–666, 1996.

Liapis H, Crouch EC, Grosso LE, Kitazawa S, Wick MR. Expression of parathyroid–like protein in normal, proliferative, and neoplastic human breast tissues. *Am J Pathol* 143: 1169–1178, 1993.

Mosely JM, Kubota M, Diefenbach–Jagger H, Wettenhall REH, Kemp BE, Suva LJ, Rodda CP, Ebeling PR, Hudson PJ, Zajac JD, Martin TJ. Parathyroid hormone–related protein purified from a human lung cancer cell line. *Proc Natl Acad Sci USA* 84: 5048–5052, 1987.

Mundy GR. Malignancy and hypercalcemia. In Calcium Homeostasis—Hypercalcemia and Hypocalcemia. Second Editor, Martin Dunitz, London, 1990.

Powell GJ, Southby J, Danks JA, Stillwell RG, Hayman JA, Henderson MA, Bennett RC, Martin TJ. Localization of parathyroid hormone–related protein in breast cancer metastases—increased incidence in bone compared with other sites. *Cancer Res* 51: 3059–3061, 1991.

Southby J, Kissin MW, Danks JA, Hayman JA, Moseley JM, Henderson MA, Bennett RC, Martin TJ. Immunohistochemical localization of parathyroid hormone–related protein in human breast cancer. *Cancer Res* 50: 7710–7716, 1990.

Stewart AF. PTHrP(1–36) as a skeletal anabolic agent for the treatment of osteoporosis. *Bone* 19:303–306, 1996.

Strewler GJ, Stem PH, Jacobs JW, Eveloff J, Klein RF, Leung SC, Rosenblatt M, Nissenson RA. Parathyroid hormone–like protein from human renal carcinoma cells: structural and functional homology with parathyroid hormone, *J Clin Invest* 80: 1803–1807, 1987.

Suda N, Gillespie MT, Traianedes K, Zhou H, Ho PWM, Hards DK, Allan EH, Martin TJ, Moseley JM. Expression of parathyroid hormone–related protein in cells of osteoblast lineage. *J Cell Physiology* 166:96–104, 1996.

Vargas SJ, Gillespie MT, Powell GT, Southby J, Danks JA, Moseley JM, Martin TJ. Localization of parathyroid hormone–related protein mRNA expression in breast cancer and metastatic lesions by in situ hybridization. *J Bone Min Res* 7: 971–979, 1992.

Vickery BH, Avnur Z, Cheng Y, Chiou SS, Leaffer D, Caufield JP, Kimmel DB, Ho T, Krstenansky JL. RS–66271, a c–terminally substituted analog of human parathyroid hormone–related protein (1–34), increases trabecular and cortical bone in ovariectomized, osteopenic rats. *J Bone Min Res* 11:1943–1951, 1996.

(List continued on next page.)

*Primary Examiner*—Toni R. Scheiner
*Attorney, Agent, or Firm*—Arnold, White & Durkee

[57] ABSTRACT

A cell-based assay technique for identifying and evaluating chemical compounds and agents which affect the production of PTH-rP in mammalian cells and other cell types is set forth. Specifically, tumor cell lines are transformed with an expression vector comprising a DNA sequence encoding a promoter region of PTH-rP operatively linked to a reporter gene encoding an assayable product and cultured under conditions which permit expression of the assayable product. Chemical agents and factors can then be identified by their ability to modulate the expression of the reporter gene, thereby affecting the production of the assayable product. Such agents are then tested for inhibitory effects on tumor cell growth and for stimulatory effects on bone formation and repair.

17 Claims, 10 Drawing Sheets

OTHER PUBLICATIONS

Vortkamp A, Lee K, Lanske B, Segre GV, Kronenberg HM, Tabin CJ. Regulation of rate of cartilage diferentiation by indian hedgehog and pth–related protein. *Science* 273:613–622, 1996.

Wysolmerski JJ, Vasavada R, Foley J, Weir EC, Burtis WJ, Kukreja SC, Guise TA, Broadus AE, Phillbrick WM. Transactivation of the PTH–rP gene in squamous carcinomas predicts the occurrence of hypercalcemia in athymic mice. *Cancer Res* 56: 1043–104, 1996.

Yin JJ, Taylor SD, Yoneda T, Dallas M, Boyce BF, Kumagai Y, Mundy GR, Guise TA. Evidence that parathyroid hormone–related protein (PTH–rP) causes osteolytic metastases without hypercalcemia. *J Bone Min Res* 10 (Suppl 1) #122, 1995.

*The Merck Index*, p. 1593, XP–002068022, Budavari, ed., 1996, Merck Research Laboratories, Whitehouse Station, NJ, USA.

*The Merck Index*, No. 22, XP–002068023, Budavari, ed., 1996, Merck Research Laboratories, Whitehouse Station, NJ, USA.

Alam and Cook, "Reporter Genes: Application to thae Study of Mammalian Gene Transcription," *Anal Biochem*, 188:245–254, 1990.

Casey et al., "Regulation of Parathyroid Hormone–Related Protein Gene Expression in Human Ednometrial Stromal Cells in Culture," *J Clin Encrocrinol Metab*, 77(1):188–194, 1993.

Yu et al., "Vitamin D analogs: new therapeutic agents for the treatment of squamous cancer and its associated hypercalcemia", *Anti–Cancer Drugs*, 6:101–108, 1995.

Mangin, et al., Mol. Endocrinol., vol. 4, No. 6, pp. 851–858, Jun. 1990.

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 4348 base pairs
      (B) TYPE: nucleic acid (C) STRANDEDNESS: single
        (D) TOPOLOGY: linear (xi) SEQUENCE DESCRIPTION: SEQ ID NO:1:

```
AGGATCCCAT CAGCTTGATG CATATCTATA CACTCCTCCC TGAGGCAGTT CCTCCAGAGG        60

TTAGCAGCCC GCCCTGTTCC TGGAGAAGTC TTATCCTCAC CTAACTACAA AAAGCATTTA       120

ATAAAGAAAC ACACCCTTTC CTATTGTTAC TTGGGGTTTG AAGGCATTAC ATCTTTTTTT       180

CTTTTTTGCT ACCTTGAGGT CAGCTGGCAA CAGCCTCCTC TCAAGTCTCA GTCCAGGCGA       240

GCGATGAGAG CCACATTCTA ATGGAATCCA ATGAGAGCAT TACTTGAGCT GATTATGCAA       300

CGTCTCTTTG TAAACATTGA AAAAGTTTG GAGAAGAGAT GGGATGAGTT TAGTTGTTTG        360

GTTCCAGGGG ATTTTAGAGA CATACGTTGC AGCTACAGAT TGGTAAATGT GAAATCTGGA       420

TGCTTATTGG TAATAAGAGA ATTCCCAAGC CCAGGTGCAC TGTTTAAAGT GCTATAGATT       480

CATATTTGGT TTATAATGTA TATCTGTTTG CTGTTTGGGT TAAGGAGGAA AGAAGAAAGA       540

AGGATGAAGA GGCTAAGCAT AAATGCTATT TACTTTTTTC TAAGCTATGA CAGGAGATAT       600

ACATTAACTG GTATTCAAC TGAATTTAAG AGTAATGCAT TTAAAATTTT TTCAACCTCT        660

ATTAAAATTT GATATACTGT AATAAACTGC CACTGGGAT GGGAAGATGG AAGCCTGGTG        720

CTCATGGGCT AGGCATTTGT GTAGGTGTAG ATCTTATAAT GCTAAACATG GAAATACTTC       780

AGATTAGAGG CAGGCCTCCC ATTTGCTAAG GTGCATTTAC ATGACAGCAA GGCCTAAGCA       840

AACATTTAGC TTCTATTGGC ACTTGTTCTA TTTCTAAACC TTAGAAAAAA GGTGTGTGTG       900

TGGGCTGGGG GGACGGGGGG GGGAGGGAGG TGGTAGGGGG TGCTCTTGCT GTGTCTCATT       960

TGCAGTCATG CATCCTCTGC ATTATTATGA TGGAGATTAC TCAGTTATGT TAGGAACTAG      1020

ATTATGATGT CAGAAAATAT CCTTTCCAAA ACAGGCAAAA AGTCAGGGTC CTGGGTATAT      1080

ATTGAGGAGA ATTTCTACGG AAAGTAATAA ACAGGGCAGC TTGGAAGAGG TACCTGCTTT      1140

CTAATAATTG CCTTTAGTGG GAACAGAAGT CTCCTTTCAA GAAGCTTTTA ATTCATTTTA      1200

AGATTTATTT TTATGTTTTC TGAAGAACAA CAAAAAATAT TTCTGGAAAA GACTGCTGAG      1260

AAGATTTCCC TCTTTCAGCC AGAAGAGCAG AGAGAAGATT GTAAATCAAG GAAAAGGTGA      1320

AGTAATAAAT TAGGAGGGAA CTTTGGTATT CCGAGTATAT AAAGACTATT TATTTTTCCT      1380

GTGTCTATAT TTTCTCTTTT TGTGGAGGAG AGGAAATTCT AAAAATATTT GATAGATGTT      1440

TTGCCATTAA CACCAGAAAA GTGTGTGGGG AAAAAGAAAG GAGGGAAGGA GTGGGGGGTT      1500

AATTTTGTTT AATTAGTAGA AAAAGCAACA TAAATCAAAG CAGTCTATTG ATGCCAGTCC      1560

TTAATTTATA ATGTTCTGAA AGTAAAGTGA ATTTATTTAC AACATAAGTG ATTTGATAAT      1620

TTCAATTTGA TTTTTGTTTT AACCTTCTAT TGGGAGAAGG GTTGACTTTT TAAAGCCTGG      1680

ATAGTTTGAA ACTTGGCTAG GTACCTTGGA CTTTTTATTG TGGAAGCAAA TATTATCATT      1740

TCAATGTTAA ACAACTTGCA AGTATTAAAT GGCTCATTTG TGATTGACTT TTTTTTTTTT      1800

TTTTTTTTTT TTTACAGAT TTCCCCCTTC AGATCTAACG ATTACATTAG GGCTCCTGCA       1860

TCTTTTTGGA AGGATTCTTT TTATAAATCA GAAAGTGTTC GAGGTTCAAA GGTTGACATT      1920

TCTGAGTGCT GATACTTTGT CCTTTCATAC TATCCAAACA AGTCTAACAT TTAGAAATCC      1980

TTACACATTC AAGGGAAGTT GTGGAAATTC CAGAGAGAG AGTGTGTGTG TGTGCGTGTG       2040

TGTGTTTTGG TTTTGTTTTG CTTTTTTTCT TTGTTAGTGA GAAGAAGCCG AGTCTTTTAA      2100

GGTACGGGGT TTACAGTAAT GAACTGAGGA AGGCAGGAGG CTTCTAAGAA AATATGCCCC      2160

CCCACCCAAC CTAAGCAGTA AACTTTAACT GCTAGCTAGC TGCAGTGAAC CAGTGGGAGC      2220

CCCGATGAGC GAGGGTCTCG GTGACAGCGT GCTATTTCTC CCACCCTGGG TAAAATATGT      2280
```

```
GGAGCATCAC CCGGAAAGTC GGGCTTGATA AAGGCCACAT TCCTTGAATC ATCTCAAGAA    2340

TCTAAATCAC ACTAGCCTTC TAGAAACTAA TGAACCCTAC CAGCAGGATT GCCTAGAAGA    2400

CAAATATCCC TTGAATGGTT CCCAGTCCAC TCGCGCTCTT TTCAAAAAGT TAGAGGAGCC    2460

CTGGGGAGGG TATCCACTCC CGCTGCAATC CTTTCCTAGA TGATACTACC CAGTAATTCC    2520

GAGCAGTCTT TCTTCCCCGC CCATTAGCTT TGGAAAGAAC CTCGGCTTTC CCGTCGCTTC    2580

TCCCAGGCAG AGCAGCACAT AACCATAGTT CCACTGCATC TGTCCGCTGG CTGCAGCGAC    2640

TCGGATACAG TCTTCCAAGA ATCTGTAACC TGGGACTTTT GAGGGGGAGG GGACAAGCAG    2700

GTAGGGTATC AGAGAAAGGA TGGGTTAGAC TCCCGACCAT GAGTGAAAAG GGCCGTGTGC    2760

GTGCTCCAGG AGTGTCGGTC CCCCTCTGCA ATTCAAAAGG GGGATCTCTC CTGTGCGCGG    2820

GTTTTTTGGG ACCGGCTCCA GATGTCTCCC AGCAGTTCTG AAACAGCAAA AAGTGCAATT    2880

TAGATATGAA ATCTGGAACT GTTTTTGTTC TTCTAAGCAA AAGATCTCCC TCTCTCTAGC    2940

CGATGCTCCC CACTCAGTTC ATCCCGGGAA TGGGCCAGGG AGGAAGGTTC TCATGCATCG    3000

CCCCGAGCTG CCAGGCGAGC TTCGGGCTCC TTAAATTCAC AGGCCAACAG CCCGCGTCCT    3060

CTCCGCGCAG GCTCCCGGTT GCCCGCGGTC CCCGGCCCAG CTCCTTGGCC TCCTCCTCGT    3120

CGGTCCGCCC CTGGTGGTCT TGGCGCCCGC TCGTCCAGCT CGGCGCGCCG GGACCGCCG     3180

GCTGCCCGGG GCAGTCCGCA CGCCCTCGGG GATCTCGGCT CCCGGATCCG CCGCGCCGGC    3240

AGGAGCCGGC CGGGCCTGGA GGGAGCAAGC GGATGCGCCC ACGCCCCGG CACGGGGATG     3300

GCGCGACAGG GCCCGGGCTC CGGGGTGGGG CTCGGCAGAG CTCCTGACAG CTCCGGGGCT    3360

CGGCAGCGCG GGAGGGGGGA GCTCCGCCGC TCGCCGCTCA TTCCCGGCTC GGGGCTCCCC    3420

TCCACTCGCT CGGGCGGCGC GGGGCCCGTT CGGGCCGCCC GTCGCCGCCC CCGCCCCCCG    3480

CGCGCCCGCC CGCCAGCCCG CCTGCGCCCT CGCTCGCCCC GCGCGCGTTC CTAGGGCGCC    3540

ACCTCTTTGC GACTAGCTCA CTTCTCCGGC AGGTTTGCCT CGGAGCGTGT GAACATTCCT    3600

CCGCTCGGTT TTCAACTCGC CTCCAACCTG CGCCGCCCGG CCAGCATGTC TCCCCGCCCG    3660

TGAAGCGGGC TGCCGCCTCC CTGCCGCTCC GGCTGCCACT AACGACCCGC CCTCGCCGCC    3720

ACCTGGCCCT CCTGATCGAC GACACACGCA CTTGAAACTT GTTCTCAGGG TGTGTGGAAT    3780

CAACTTTCCG GAAGCAACCA GCCCACCAGA GGAGGTAGAC AGACAGCTAT GTATATATAT    3840

GTGGGTTTCG CTACAAGTGG CTCTGGAACG AAAGGGCCTG GTTCGCAAAG AAGCTGACTT    3900

CAGAGGGGGA AACTTTCTTC TTTTAGGAGG CGGTTAGCCC TGTTCCACGA ACCCAGGAGA    3960

ACTGCTGGCC AGATTAATTA GACATTGCTA TGGGAGACGT GTAAACACAC TACTTATCAT    4020

TGATGCATAT ATAAAACCAT TTTATTTTCG CTATTATTTC AGAGGAAGCG CCTCTGATTT    4080

GTTTCTTTTT TCCCTTTTTG CTCTTTCTGG CTGTGTGGTT TGGAGAAAGC ACAGTTGGAG    4140

TAGCCGGTTG CTAAATAAGT AAGTGCTGAG AGGCTCCAGA GAAATTTTTT TTCTTTTCAA    4200

CTTGGGAGAT GCCCTTGATG TTGAAGAGGC TTTTTGAGAG CGGGCTAAAA AGGGGGAGCG    4260

GAGTAGTGCG GGGAGATGGA GAGTCCTGAC TGACACCTCG GGTCCCATTC CCTTCTGTTG    4320

CAGGTCCCGA GCGCGAGCGG AGACGATG                                      4348
```

SCREENING ASSAY FOR THE IDENTIFICATION OF AGENTS WHICH ALTER EXPRESSION OF PTH-RP

This application claims priority on provisional application U.S. Ser. No. 60/025,215, filed Aug. 23, 1996.

FIELD OF THE INVENTION

The present invention relates generally to methods for screening compounds for their ability to affect the production of certain peptides which are destructive to those cells and to organisms, in some situations, but may be beneficial to those cells and organisms in other situations. More specifically, the invention relates to a method of identifying compounds from sources such as small molecule chemical libraries, peptide libraries and from natural product collections which inhibit the production of peptides related to bone destruction in patients with cancer, especially metastatic breast cancer. Furthermore, the invention as described specifically above may be used to identify compounds from said sources that stimulate the production of peptides related to bone formation and repair.

RELATED ART

Solid tumors such as breast cancer and lung cancer cause bone destruction by spreading to the bone marrow cavity, where tumor cells accumulate, grow and cause progressive bone destruction. These destructive bone lesions are known as osteolytic metastases and are responsible for complications in patients with cancer such as bone pain, pathologic fractures, hypercalcemia and nerve compression syndromes (Mundy, 1990).

One of the mechanisms by which breast cancer cells cause bone destruction is by producing the tumor peptide parathyroid hormone-related protein (PTH-rP). This protein was purified in 1987 simultaneously by several independent groups from human lung cancer (Moseley et al., 1987), breast cancer (Burtis et al., 1987) and renal cell carcinoma (Strewler et al., 1987). Apparently, PTH-rP production in tumor cells is induced by high levels of TGF-β found in bone tissue.

Recent evidence supports the hypothesis that PTH-rP is important in the bone destruction mediated by breast cancer and other tumors which metastasize to bone. In breast cancer, PTH-rP was detected by immunohistochemical staining in 60% of 102 invasive breast cancers removed from normocalcemic women, but not in normal breast tissue (Southby et al., 1990). At least two other studies have confirmed these findings (Liapis et al., 1993; Bundred et al., 1992). By immunohistochemistry (Vargas et al., 1992) and in situ hybridization (Powell et al., 1991), PTH-rP was detected in 12 out of 13 breast cancer metastases in bone leading to the conclusion that production of PTH-rP locally in bone may be responsible for the bone destruction associated with metastatic breast cancer.

Bundred and colleagues found positive immunohistochemical staining for PTH-rP in 56% of 155 primary breast tumors from normocalcemic women and PTH-rP correlated with development of bone metastases (Bundred et al., 1992). PTH-rP expression was detected by reverse transcriptase-PCR in 37 out of 38 primary breast cancers, and subsequent development of bone metastases was associated with greater PTH-rP expression (Bouizar et al., 1993). Thus, PTH-rP expression appears to be common in breast cancers once they have metastasized to bone.

More recently, Yin et al. (1995) have studied the capacity of breast cancer cells to produce PTH-rP in the bone microenvironment using established cultures of human breast cancer cell lines. These workers found that 4 of 8 established human breast cancer cell lines expressed detectable PTH-rP, and one of these PTH-rP secreting cell lines, MDA-MB-231, was studied in detail using an in vivo model of osteolytic metastases. In this model, cancer cells are inoculated into the left ventricle of the heart of nude mice and the development of osteolytic metastases was followed by radiology and histology 3–6 weeks later. These workers found that there was increased PTH-rP concentrations in bone marrow plasma taken from the femurs of mice with osteolytic lesions, a 2.5-fold increase over corresponding plasma PTH-rP concentrations. This indicates local production of PTH-rP in the bone micro-environment. Moreover, when they investigated the functional role of PTH-rP by inoculating the mice with neutralizing antibodies to PTH-rP, and compared them with mice receiving control IgG or no treatment, they found not only decreased osteoclast number/$mm^2$ of tumor-bone interface and increased bone area, but also decreased tumor area in tumor bearing animals treated with PTH-rP antibodies compared with corresponding controls. These results show that tumor-produced PTH-rP may cause local bone destruction in human breast cancers which metastasize to bone. Moreover, they show that neutralizing antibodies to PTH-rP reduce tumor burden in bone.

Clearly, PTH-rP production by tumor cells contributes in the pathogenic process of bone metastasis. It would, therefore, be highly desirable to identify compounds which inhibit PTH-rP production, thus halt progressive bone destruction and improve the quality of life of patients with cancer. Thus, there is a need for techniques for detecting chemical compounds that decrease the production of PTH-rP by cancer cells.

PTH-rP influences a number of biological processes. Perhaps the most important is endochondral bone formation. PTH-rP is known to be essential for normal cartilage differentiation and endochondral bone formation. Deletion of the PTH-rP gene by introducing the null mutant into the germ line results in mice with impaired skeletal development and enhanced endochondral ossification (Karaplis et al, 1994). PTH-rP is a negative regulator of endochondral bone formation and terminal cartilage cell differentiation. This effect is possibly mediated by Indian Hedgehog protein which is made by pre- and early hypertrophic cells and stimulates production of PTH-rP in the perichondrium (Lanske et al, 1996; Vortkamp et al, 1996). Thus PTH-rP likely has an important role in normal endochondral bone formation and possibly also in fracture repair and therefore altering rates of PTH-rP expression may influence not just bone formation but also fracture repair, and such compounds could be administered to enhance the fracture repair process PTH-rP also is produced by osteoblasts in the bone microenvironment. This has been demonstrated in osteoblast cultures as well as in organ cultures of rat long bones (Suda et al, 1996). PTH (and PTH-rP) have powerful anabolic effects on bone (Stewart 1996; Vickery et al, 1997), and therefore enhancing local production of PTH-rP in the bone microenvironment by compounds which increase its transcription cause anabolic effects in this microenvironment.

SUMMARY OF THE INVENTION

The present invention addresses the foregoing need by providing a cell-based assay for identifying compounds which affect PTH-rP production. Specifically, the invention comprises culturing a cell containing an expression vector comprising a DNA sequence encoding a PTH-rP promoter operatively linked to a reporter gene, namely firefly luciferase, under conditions which permit expression and quantitative assay of the reporter gene. The cultured cell is incubated with compounds suspected of possessing regulatory activity for production of PTH-rP. These inhibitory compounds are identified by their ability to modulate the expression of the reporter gene and thereby affect the production of the assayable product of the reporter gene.

In a general embodiment, the present invention provides a method for screening a compound for its ability to affect PTH-rP production in mammalian cells. The method comprises the following steps:

(a) providing an expression construct comprising a PTH-rP promoter and a reporter gene, wherein the reporter gene is under transcriptional control of the promoter;

(b) transfecting the mammalian cells with the expression construct (c) contacting the transfected cell with the compound; and (d) identifying a compound that regulates expression of the reporter gene from the promoter.

In a preferred embodiment, the reporter gene is selected from the group consisting of firefly luciferase, chloramphenicol acetyl transferase, β-galactosidase, green fluorescent protein, human growth hormone, alkaline phosphatase and β-glucuronidase. In a most preferred embodiment, the reporter gene is firefly luciferase.

In a further preferred embodiment, the promoter for PTH-rP is derived from the native PTH-rP promoter. Promoter sequences (P1, P2 and P3) are shown SEQ ID NO:1. A particularly effective expression construct is the plasmid pGL3B-PTH-rP 1.1, containing the P2 and P3 promoters.

It is preferred that the present invention be used to screen a compound for its ability to regulate PTH-rP production in human cells. A particularly useful cell population to use in screening for PTH-rP inhibition is human tumor cells. Most notably, the present invention is useful in screening compounds which affect PTH-rP production in breast cancer cells. A particularly useful breast cancer cell population in which to perform screening are MDA-MB-231 cells. Another especially preferred cell population for screening compounds which affect PTH-rP production are lung cancer cells. A particularly useful cell population in which to perform screening are RWGT2 cells. Another especially preferred cell population for screening compounds which affect production of PTH-rP are bone cells. A particularly useful cell population in which to perform screening are bone cells selected from the group consisting of MC3T3-E1, MG-63, U2OS, UMR-106, ROS17/2.8 and SAOS-2.

In another general embodiment, the present invention provides compounds that affect PTH-rP production in mammalian cells. This compound is identified by the method comprising the steps of:

(a) providing an expression construct comprising a PTH-rP promoter and a reporter gene, wherein the reporter gene is under transcriptional control of the promoter;

(b) transfecting the mammalian cells with the expression construct;

(c) contacting the transfected cell with the compound; and (d) identifying a compound that regulates expression of the reporter gene from the promoter.

Preferably, the compound is identified from a small molecule chemical library, a peptide library, or from a collection of natural products. In a preferred embodiment, the compound is OSWs1, OSW3, OSW6 and analogs thereof including but not limited to:

6-chloro-9-(tetrahydro-2-pyranyl) purine
6-methyl purine riboside
6-(β-hydroxyethylamino) purine
6-methylmercapto purine
9-(2-tetrahydropyranyl) adenine
8-aminoguanosine
6-(_,_-dimethylallylamino) purine
6-(_,_-dimethylallylamino) purine riboside
cis-zeatin
6-(1-hydroxyguanidino) purine riboside
purine
purine riboside
aristeromycin
zeatin
n-benzyl-9-(2-tetrahydropyranyl) adenine
8-azaxanthine
8-aza-2,6 diamino purine
8-azaadenine
8-azaguanine
2-amino-6-(alpha-carboxyethyl)-mercapto purine
2-amino-6-(1'-methyl-4'-nitro-5'-imidazoyl) mercapto purine
2-amino-6-mercapto purine riboside (6-mercaptoguanosine)
2-mercaptopurine (2-thiopurine)
2-thioxanthine (6-hydroxy-2-mercapto purine)
6-mercapto purine
6-mercapto purine-2'-deoxyriboside
6-mercapto purine riboside
6-mercapto purine riboside 5'-phosphate (thioinosinic acid)
6-mercapto purine arabinoside
6-thioxanthine (2-hydroxy-6-mercapto purine)
2',4'-O-isopropylidene-6-mercapto purine riboside Finally, yet a third embodiment of the present invention provides a method of regulating PTH-rP production in mammalian cells. This method comprises the step of contacting a cell with a compound that affects PTH-rP production in the cell. Preferred compounds are OSWs1, OSW2, OSW3, OSW4, and OSW6 and analogs thereof and dexamethasone.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
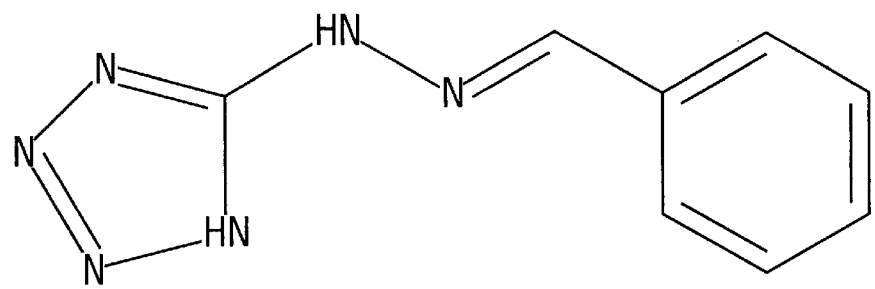
FIG. 1 shows the compound 5-benzylidene hydrazino-1,2,34-tetrazole, known as OSW3.
Figure 2:
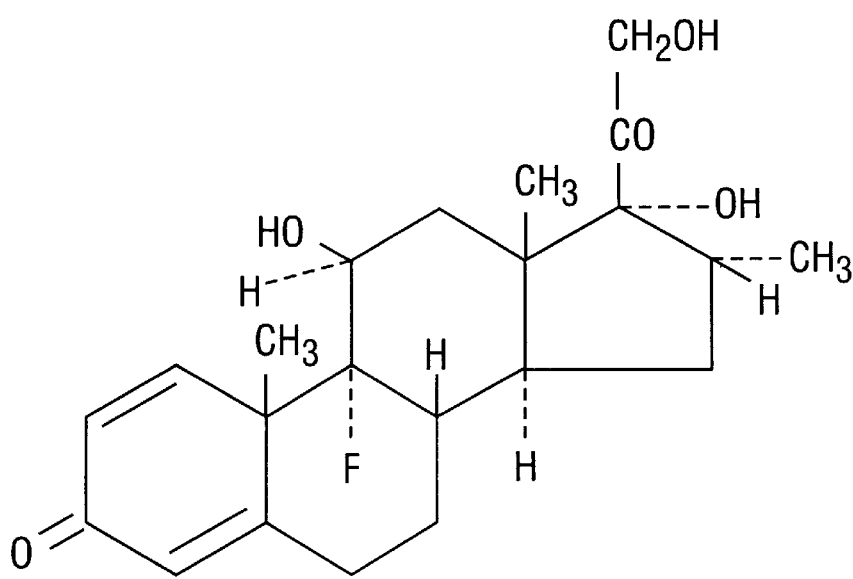
FIG. 2 shows the compound 2-(2-carboxypyrid-2-yl)-4-methyl-4-propylimidazolidin-5-one(HCl), known as OSW2.
Figure 3:
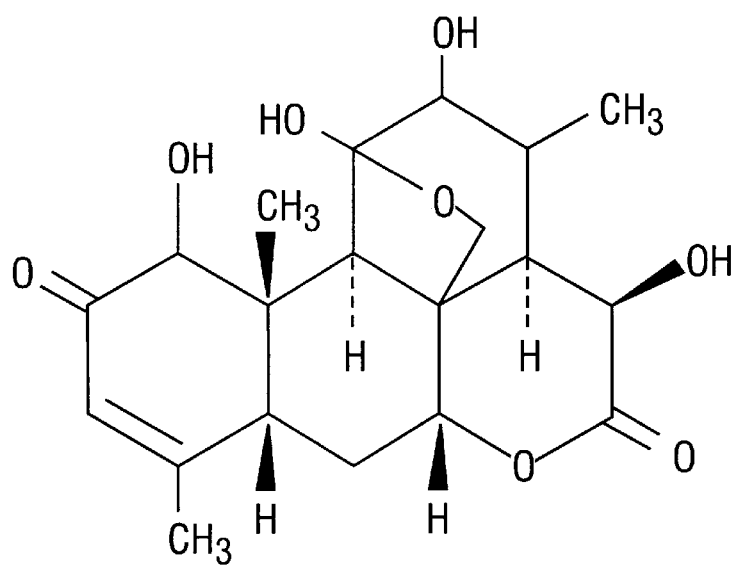
FIG. 3 shows the compound glaucarubolone, known as OSW4.

As stated above, evidence suggests a role for PTH-rP in certain cancers along with bone formation and repair. The present invention involves a cell-based assay technique for identifying and evaluating chemical compounds and agents which affect the production of PTH-rP, thereby identifying chemotherapeutic compounds for use in the treatment of cancer. This cell-based assay also is believed to work equally well in assessing compounds for their inhibition of PTH-rP production in a variety of cancers including lung, bone and breast cancers. Furthermore, this cell-based assay is believed to work equally well in identifying compounds for their stimulation of PTH-rP production, thereby identifying therapeutic compounds for the use in bone repair (e.g., after bone fracture).

Specifically, cells are transfected with an expression vector comprising a DNA sequence encoding a promoter region of PTH-rP operatively linked to a reporter gene encoding an assayable product. The cells are then cultured under conditions which permit expression of the assayable product. The PTH-rP promoter region is preferably cloned from genomic DNA but may be synthesized de novo. A preferred expression vector construct is the plasmid pGL3B-PTH-rP1.1 containing a PTH-rP promoter and the gene for firefly luciferase as the reporter gene.

After transfection with the expression vector, the cells are incubated with at least one compound suspected of possessing regulatory activity for PTH-rP expression. Chemical agents and factors can be identified by their ability to modulate the expression of the reporter gene and thereby increase or decrease the production of the assayable product. Such chemical compounds are selected from small chemical libraries, peptide libraries, and/or collections of natural products.

The present invention is distinguished from other techniques for identifying chemical compounds, as it specifically identifies chemical compounds, agents, factors and other substances which affect PTH-rP production by cells. These agents are identified by their capacity to affect the activity of PTH-rP promoters. Decrease in activity of the promoters is measured by a correspondent decrease in production of the reporter gene's product. Increase in activity of the promoters is measured by a correspondent increase in production of the reporter gene's product. Thus, decrease in the production of, for example, firefly luciferase, indicates that PTH-rP promoter activity is being suppressed by the compound being tested; an increase in the production of firefly luciferase in indicative of stimulation of the PTH-rP promoter. The affect in production of the assaying product reflects the affect in PTH-rP that would occur in a cell treated with the compound.

Ultimately, when cancer patients are treated with chemical compounds shown to decrease PTH-rP promoter activity, PTH-rP production by tumor cells will be inhibited, resulting in decreased bone destruction and impaired growth of the tumor in bone tissue. Therefore, compounds identified by this assay technique that decrease PTH-rP promoter activity can be used in the treatment of cancers which metastasize to bone and cause hypercalcemia, and other conditions where PTH-rP production is excessive and harmful.

When patients requiring bone formation or repair are treated with chemical compounds shown to increase PTH-rP promoter activity, PTH-rP production by osteoblasts will be stimulated, resulting in bone formation and repair. Therefore, compounds identified by this assay technique that increase PTH-rP promoter activity can be used in the treatment of bone trauma, underdevelopment of the bone, and other conditions where PTH-rP production is desired.

A. PTH-rP Promoter

A technique often employed by those skilled in the art of protein production today is to obtain a "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved, for purposes of the present invention, by cloning of a genomic DNA molecule containing a PTH-rP promoter. Alternatively, having knowledge of the PTH-rP promoter sequence, the promoter may be synthesized according to standard techniques.

The first step in a cloning procedure is the screening of an appropriate DNA library, such as, in the present case, a tumor-derived library. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature.

Three PTH-rP promoters are contained within a 4.3 kB genomic DNA upstream from the start site of the PTH-rP gene, located on chromosome 12. The three promoters are as follows: P1 is 5' of exon 1A (the upstream TATA element); P2 is 5' of exon 1C (the midregion GC rich element); P3 is 5' of exon 2 (downstream TATA element). Three isoforms of PTH-rP have been identified, which are 139, 141 and 173 amino acids in length. All three isoforms have the same amino acid sequence through residue 139. The isoforms arise from alternative 3' splicing. Their relative secretory rates and their relative importance to normal and pathophysiology have yet to be fully elucidated. However, most, and possibly all tumors expressing PTH-rP express PTH-rP 1-141 driven by P3.

Constructs employed are pGL3B-PTHrP 1.1 and pGL4B-PTHrP 4.0, the former incorporating promoters P2 and P3 and the latter incorporating all three promoters. A 4345 bp fragment of the PTH-rP promoter region is set forth in SEQ ID NO:1.

B. Reporter Genes

A reporter gene is a gene which produces a product having a readily identifiable and assayable phenotype. The gene encoding firefly luciferase (Promega, Madison, Wis.) is particularly useful in the present invention because the gene produces an easily quantifiable, visually detectable enzyme. One skilled in the art will however recognize other useful reporter genes which will work equally well in the present invention. Examples of such reporter genes include, but are not limited to, chloramphenicol acetyl transferase (Promega), β-galactosidase (Promega), green fluorescent protein (Clontech, Palo Alto, Calif.), human growth hormone (Amersham Life Science, Arlington Heights, Ill.), alkaline phosphatase (Clontech) and β-glucuronidase (Clontech).

C. Expression Constructs

The expression constructs, commonly referred to as vectors, that can be utilized in the disclosed cell-based assay of the instant invention may vary considerably. The vectors may be "standard" expression vectors, i.e., plasmids that contain one or more effector genes and regulatory elements required for expression of the effector gene in cells. Plasmid expression vectors include any plasmid, cosmid or phage construct that is capable of supporting expression of encoded genes in mammalian cells, such as pUC or Bluescript™ plasmid series. Alternatively, these vectors may be more complex, such as the viral vectors discussed below.

The regulatory elements of an expression vector will comprise at least a promoter, in this case the PTH-rP promoter and a reporter gene (as discussed above), and also may include structures that assist in replication, such as origins of replication. In addition, almost all expression vectors contain multipurpose cloning regions that have numerous restriction enzyme sites. One also typically will include a polyadenylation signal to effect proper polyadenylation of the transcript. The nature of the polyadenylation signal is not believed to be crucial to the successful practice of the invention, and any such sequence may be employed. Examples include SV40 and bovine growth hormone poly-A sites. Also contemplated as an element of the expression construct is a terminator. These elements can serve to enhance message levels and to minimize read through from the construct into other sequences. Finally, expression vectors typically have selectable markers, often in the form of antibiotic resistance genes, that permit selection of cells that carry these vectors.

As stated above, in certain embodiments of the present invention, the expression construct-comprises a virus or engineered construct derived from a viral genome. The ability of certain viruses to enter cells via receptor-mediated endocytosis and, in some cases, integrate into the host cell chromosomes, have made them attractive candidates for gene transfer in to mammalian cells.

i. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol, and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and by enhancer sequences and are also required for integration in the host cell genome (Coffin, 1990).

In order to construct a retroviral vector, a nucleic acid encoding a PTH-rP promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human cDNA, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

ii. Adenoviruses

Human adenoviruses are double-stranded DNA tumor viruses with genome sizes of approximate 36 kB (Tooze, 1981). As a model system for eukaryotic gene expression, adenoviruses have been widely studied and well characterized, which makes them an attractive system for development of adenovirus as a gene transfer system. This group of viruses is easy to grow and manipulate, and exhibit a broad host range in vitro and in vivo. In lytically infected cells, adenoviruses are capable of shutting off host protein synthesis, directing cellular machinery to synthesize large quantities of viral proteins, and producing copious amounts of virus.

The E1 region of the genome includes E1A and E1B which encode proteins responsible for transcription regulation of the viral genome, as well as a few cellular genes. E2 expression, including E2A and E2B, allows synthesis of viral replicative functions, e.g. DNA-binding protein, DNA polymerase, and a terminal protein that primes replication. E3 gene products prevent cytolysis by cytotoxic T cells and tumor necrosis factor and appear to be important for viral propagation. Functions associated with the E4 proteins include DNA replication, late gene expression, and host cell shutoff. The late gene products include most of the virion capsid proteins, and these are expressed only after most of the processing of a single primary transcript from the major late promoter has occurred. The major late promoter (MLP) exhibits high efficiency during the late phase of the infection (Stratford-Perricaudet and Perricaudet, 1991).

As only a small portion of the viral genome appears to be required in cis (Tooze, 1981), adenovirus-derived vectors offer excellent potential for the substitution of large DNA fragments when used in connection with cell lines such as 293 cells. Ad5-transformed human embryonic kidney cell lines (Graham, et al., 1977) have been developed to provide the essential viral proteins in trans. The characteristics of adenoviruses rendered them good candidates for use in gene transfer both in vitro and in vivo (Grunhaus & Horwitz, 1992).

Particular advantages of an adenovirus system for delivering foreign proteins to a cell include (i) the ability to substitute relatively large pieces of viral DNA by foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible (Grunhaus & Horwitz, 1992).

In general, adenovirus gene transfer systems are based upon recombinant, engineered adenovirus which is rendered replication-incompetent by deletion of a portion of its genome, such as E1, and yet still retains its competency for infection. Sequences encoding relatively large foreign proteins can be expressed when additional deletions are made in the adenovirus genome. For example, adenoviruses deleted in both E1 and E3 regions are capable of carrying up to 10 kB of foreign DNA and can be grown to high titers in 293 cells (Stratford-Perricaudet and Perricaudet, 1991). Persistent expression of transgenes following adenoviral infection has also been reported.

iii. Other Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpes viruses may be employed. These viruses offer several attractive features for gene transfer into various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. in vitro studies showed that the virus could retain the ability for helper-dependent packaging and reverse transcription despite the deletion of up to 80% of its genome (Norwich et al., 1990). This suggested that large portions of the genome could be replaced with foreign genetic material. The hepatotropism and persistence (integration) were particularly attractive properties for gene transfer into liver cells. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

iv. Alternative Delivery Service

In order to effect expression of reporter gene constructs, the expression vector must be delivered into a cell. As described above, one mechanism for delivery is via viral infection where the expression vector is encapsidated in an infectious adenovirus particle.

Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), polycations (Boussif et al., 1995) and receptor-mediated transfection (Wu and Wu, 1987; Wu and Wu, 1988).

In one embodiment of the invention, the expression vector may simply consist of naked recombinant vector. Transfer of the construct may be performed by any of the methods mentioned above which physically or chemically permeabilize the cell membrane. For example, Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$-precipitated plasmids results in expression of the transfected genes. It is envisioned that DNA encoding a construct according to the present invention may also be transferred in a similar manner.

Another embodiment of the invention for transferring a naked DNA expression vector into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression vector may be entrapped in a liposome. Liposomes are vesicular structures characterized by a phospholipid bilayer membrane and an inner aqueous medium. Multilamellar liposomes have multiple lipid layers separated by aqueous medium. Liposomes form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated polynucleotide delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of a polynucleotide in vitro and in vivo, then they are applicable for the present invention. Where a bacteriophage promoter is employed in the DNA construct, it also will be desirable to include within the liposome an appropriate bacteriophage polymerase.

Another mechanism for transferring expression vectors into cells is receptor-mediated delivery. This approach takes advantage of the selective uptake of macromolecules by receptor-mediated endocytosis in almost all eukaryotic cells. Because of the cell type-specific distribution of various receptors, the delivery can be highly specific (Wu and Wu, 1993). Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1993). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that an adenoviral expression vector also may be specifically delivered into a cell type such as lung, epithelial or tumor cells, by any number of receptor-ligand systems, with or without liposomes. For example, epidermal growth factor (EGF) may be used as the receptor for mediated delivery to cells that exhibit upregulation of EGF receptor, such as tumor cells. Galactose can be used to target the asialoglycoprotein receptor on liver cells. Also, antibodies to CD5 (CLL), CD22 (lymphoma), CD25 (T-cell leukemia) and MAA (melanoma) can similarly be used as targeting moieties.

D. Cell Lines

The cells which can be utilized for transfection in the present invention include and cell that has the transcriptional machinery necessary to direct synthesis from a PTH-rP promoter. Preferred examples include the human cancer cells designated MDA-MB-231, MCF-7, RWGT2 and any other cancer cells which behave as cancer cells in vivo, i.e., produce small amounts of PTH-rP unless present in bone. In addition, a number of normal bone cell lines available commercially MC3T3-E1 cells, MG-63 cells, U2OS cells, UMR-106 cells, ROS 17/2.8 cells, SaOS-2 cells, in the catalog provided from the American Type Culture Collection (ATCC), also can be utilized for this assay.

E. Candidate Compounds

Six candidate compounds and their analogs have been identified on the basis of the assay of the present invention. Five of these compounds come from the MicroMolecular Library of MicroSource Discovery Systems, Inc. Gaylordsville, Conn.—OSWs1 (acriflavinium hydrochloride), OSW2 (2-(2-carboxypyrid-2-yl)-4-methyl-4-propylimidazolidin-5-one(HCl)), OSW3 (5-benzylidene hydrazino-1,2,34-tetrazole) and OSW4 (glaucarubolone) and OSW6 (6-thioguanine). The structures of these compounds are illustrated in FIGS. 6, 2, 1 and 3, and 5, respectively.

Figure 4:
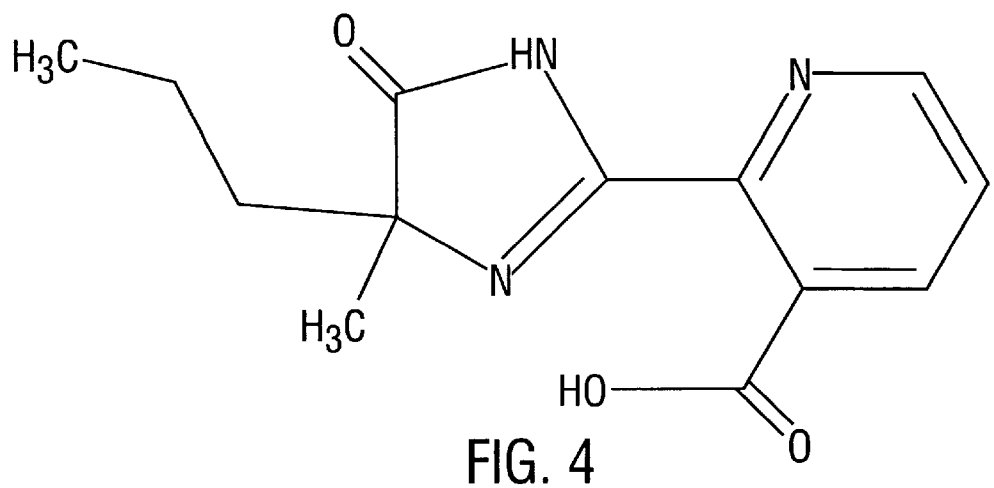
FIG. 4 shows the compound dexamethasone.
Figure 5:
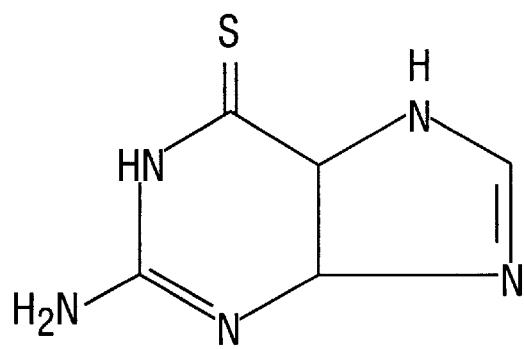
FIG. 5 shows the compound 6-thioguanine, known as OSW6.

The sixth compound is dexamethasone (pregna-1, 4-diene-3,20-dione,9-fluoro-11,17,21-trihydroxy-16-methyl-(11β,16α). The structure of this compound is illustrated in FIG. 4. Dexamethasone possesses glucocorticoid activity, for which it is used clinically. It is especially useful as an anti-inflammatory and anti-allergic drug. Topically, it is employed in the treatment of glucocorticoid-responsive dermatoses. Systematically, it decreases the incidence and severity of hearing loss subsequent to bacterial meningitis. It also is used as a diagnostic for Cushing's syndrome, lowering plasma cortisol levels in persons that do not have Cushing's. The plasma half-life is 3 to 4 hours, and the biological half-life is 36 to 54 hours.

Dexamethasone is soluble in alcohol (1 g in 42 ml) and practically insoluble in water. Formulation include aerosol (topical), elixir, gel, opthalmic suspension and tablet. Therapeutic doses range from 500 μg to 9 mg daily, usually less for maintenance, or 8 mg every other day for one month.

F. Pharmaceuticals and Methods of Treatment

In another embodiment of the present invention, there are provided methods for the treatment of cancer. The present invention contemplates the use of compounds having suppressive activity against the PTH-rP promoter and, hence, against PTH-rP in tumor cells. Treatment methods will involve treating an individual with an effective amount of a PTH-rP inhibitory compound. An effective amount is described, generally, as that amount sufficient to detectably and repeatedly reduce the level of PTH-rP in a cell.

In an another embodiment of the present invention, there are provided methods for treating bone damage or underdevelopment. The present invention contemplates the use of compounds having stimulatory activity for the PYH-rP promoter and, hence, production of PTH-rP by bone cells. Treatment methods will involve treating an individual with an effective amount of a PTH-rP stimulatory compound. An effective amount is described, generally, as that amount sufficient to detectably and repeatedly increase the level of PTH-rP in a cell.

Administration of the compound to patient will follow general protocols for the administration of chemotherapeutics, taking into account the toxicity, if any, of the compound. It is anticipated that the treatment cycles would be repeated as necessary.

Where clinical application of a PTH-rP inhibitory compound is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. Intratumoral administration may be preferred for treatment of discrete tumor masses. Similarly, direct administration into the area of bone damage or underdevelopment may be preferred for treatment of the disorders.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

Therapies according to the present invention encompass combination therapies that include treatment with anti-PTH-rP compositions as well as standard chemo- and radiotherapies. For example, chemotherapeutics include, but are not limited to, cisplatin (CDDP), carboplatin, procarbazine, mechlorethamine, cyclophosphamide, isofamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate. Also included in combined therapies may be x- and γ-irradiation.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

In the examples which follow, the following abbreviations apply: eq (equivalents); M (Molar); mM (millimolar); $\mu$M (micromolar); N (normal); mol (moles); mmol (millimoles); $\mu$mol (micromoles); nmol (nanomoles); kg (kilograms); gm (grams); mg (milligrams); $\mu$g (micrograms); $\mu$l (microliters); vol (volumes); ° C. (degrees Centigrade); FCS (fetal calf serum).

Example 1

Transfection of Tumor Cells with PTH-rP Promoter Linked to a Reporter Gene

To perform studies on the PTH-rP promoter in whole cells, a human breast cancer cell line, MDA-MB-231 (kindly provided by C. Kent Osborne, San Antonio Tex.) and a human lung cancer cell line, RWGT2, were employed. Various PTH-rP promoters, described in Wysolmerski et al., 1996, were linked with the reporter gene firefly luciferase and stably transfected into cell lines. Plasmid constructs included pGL3B-PTH-rP1.1 and pGL4B-PTHrP 4.0. RWGT2 cells and MDA-MB-231 cells were cultured in DMEM (Life Technologies, Grand Island, N.Y.) with 10% FCS (Hyclone, Logan, Utah), 0.1% penicillin/streptomycin and 0.1% nonessential amino acids (Gibco) in 37° C. atmosphere of 5% $CO_2$/air.

Before stable transfection of MDA-MB-231 cells with pGL3B-PTH-rP1.1, the concentration of geneticin (G418) required to kill MDA 231 cells was determined to be 500 μg/ml. Next, 6-well tissue culture plates were seeded with exponentially growing MDA-MB-231 cells 24 hours prior to transfection. Thirty μg pGL3B-PTH-rP1.1 was diluted with $dH_2O$ to 90 μl and 3 μg pSV2neo added. Ten μl 2.5M $CaCl_2$ was added followed by 100 μl of 2×BBS. This mixture was next incubated at room temperature for 15 minutes. The mixture was then added to MDA-MB-231 cells dropwise and swirled to distribute evenly, followed by incubation overnight at 37° C. in 3% $CO_2$. The cells were then washed twice with PBS and 3 ml DMEM 10% FCS was added and incubated overnight at 37° C. in 5% $CO_2$. After 3 days, the cells were split 1:10 and incubated for another 3 days at 37° C. in 5% $CO_2$. The cells were washed twice with PBS. DMEM 10% FCS was added containing 500 μg/ml of geneticin. The cells were passaged twice a week for three weeks and incubated at 37° C. in 5% $CO_2$. Subcloning and selection was then begun.

Subcloning consisted of diluting the geneticin resistant MDA-MB-2311 cells containing pGL3B-PTHrP1.1 to a concentration of 0.3 cells/100 μl. Cells were aliquoted in 100 μl increments into ten 96 well tissue culture plates. Colonies were allowed to grow over a period of 3 weeks and then assayed for luciferase activity. The luciferase activity was assessed by luminometer. Cell lysates were prepared and the luciferase enzyme assay was carried out using assay protocols and the assay kit from Promega (Madison, Wis.). Routinely, 20 μl of cell lysate was mixed with 100 μl of luciferase assay reagent (270 μM co-enzyme A, 470 μM luciferin and 530 μM ATP) and the luciferase activity was measured for 10 seconds in a Turner TD-20e luminometer. The values were normalized with respect to the protein concentration obtained from each experimental sample. The protein concentration was assessed using BioRed reagents. Colonies exhibiting high luciferase activity were further selected by treatment with 2.5 mM dexamethasone. One clone was chosen which exhibited high basal levels of luciferase activity and when dexamethasone was added demonstrated a 30–40% inhibition of luciferase activity. This clone (Clone 30) was used in our screening assay.

Example 2

Analysis of the Ability of Compounds to Inhibit Expression of PTH-rP In Vitro

To demonstrate that the present invention is useful in evaluating chemical compounds and agents which regulate PTH-rP production, a random array of chemical compounds obtained commercially from a library of 3840 compounds, purchased from MicroSource Inc., (New Haven, Conn.) was screened. Approximately 342 of 3840 such compounds decreased production of PTH-rP in the present assay system at a concentration of 10 μM when compared to basal control levels. Such compounds identified from the random library were then tested again at 2 doses (10 μM, 1 μM) to again demonstrate that they inhibited PTH-rP promoter-luciferase expression at both doses. These compounds were then tested for toxic effects on MDA-MB-231 cells by the capacity of 90% of the cells or more to exclude trypan blue following 10 minutes incubation with the compounds.

The five agents that satisfied these criteria (i.e., effects at both doses, nontoxic to tumor cells), were then tested for their capacity to inhibit PTH-rP production of MDA-MB-231 and RWGT2 cells as measured by RIA. PTH-rP RIA assay was carried out using assay protocols and the PTH-rP assay kit from Nichols Institute Diagnostics (San Juan Capistrano, Calif.). Routinely, 200 μl of sample was mixed with 100 μl of the $^{125}I$ PTH-RP antibody solution and allowed to incubate at room temperature for 21 hrs. An avidin coated bead was then added and 90 min later sample/antibody solution mixture was completely aspirated. Beads were washed twice and counted using a Pharmacia Gamma Counter. Two of the 432 compounds were positively identified.

Example 3

Analysis of the Ability of Compounds to Inhibit Expression of PTH-rP In Vivo. Hypercalcemia Studies Compounds which are identified as regulating PTH-rP production were initially tested for their capacity to inhibit hypercalcemia in vivo by injecting tumor cells into nude mice and treating the mice with the potential inhibitory compounds. Specifically, compounds to be tested were injected into the subcutaneous tissue, intramuscularly, or intravenously into nude mice which were also inoculated with the human cancer cells which produce PTH-rP. The effects on the capacity of the tumor cells to cause hypercalcemia are then assessed over 2–4 weeks.

To demonstrate initially that compounds inhibit PTH-rP expression in vivo, a human tumor cell which is known to overexpress PTH-rP was used. The tumor, designated RWGT2, is a human squamous cell carcinoma of the lung that was obtained from a hypercalcemic cancer patient (Guise et al, 1993). Metastatic tumor tissue was taken at the time of surgical repair of a pathologic fracture of the femur and implanted into athymic nude mice. The mice developed hypercalcemia, tumors, and increased serum PTH-rP concentrations. Tumor tissue from the mice was used to establish this cell line in culture. The cells produced PTH-rP in culture and reliably produced tumors and hypercalcemia when inoculated intramuscularly into the nude mice.

The RWGT2 cells are grown in culture in T75 flasks in α-minimal essential medium (αMEM, Hazelton Biologics Inc., Lenexa, Kans.) with 10% fetal calf serum and passaged twice a week. The mice are inoculated with RWGT2 cells by subcutaneous inoculation of $1 \times 10^6$ cells into the right flank of the upper leg.

All animal studies are conducted in accordance with the NIH Guide for the Care and Use of Laboratory Animals. Male BALB/c nude mice (Harlen), 4–6 weeks of age, are housed in a laminar flow isolator hood with a 12-hour-light/12-hour-dark cycle. Water, supplemented with multivitamins (Lymphomed, Melrose Park, Ill.) and autoclaved mouse chow (Ralston-Purina, St. Louis, Mo.) were provided ad libitum.

Weekly, the mice (each group n=5) are weighed and tumor diameters (long axis and mean axis width) are measured using calipers. Also whole blood samples for ionized calcium ($Ca^{2+}$) determination is obtained by retro-orbital puncture under anesthesia and measured using a Ciba Corning 634 ISE $Ca^{++}$/pH analyzer. Finally, blood samples for PTH-rP measurements is obtained by retro-orbital puncture and collected on ice, into pediatric vacutainer tubes containing ethylenediamine tetraacetate (EDTA) (Becton Dickinson, Rutherford, N.J.) and aprotinin (Sigma Chemical Company, St. Louis, Mo.), 400 KIU/ml and stored at −70° C. Immunoreactive PTH-rP is measured using a 2 site IRMA kit available from Nichols Institute (San Juan Capistrano, Calif.).

Figure 7:
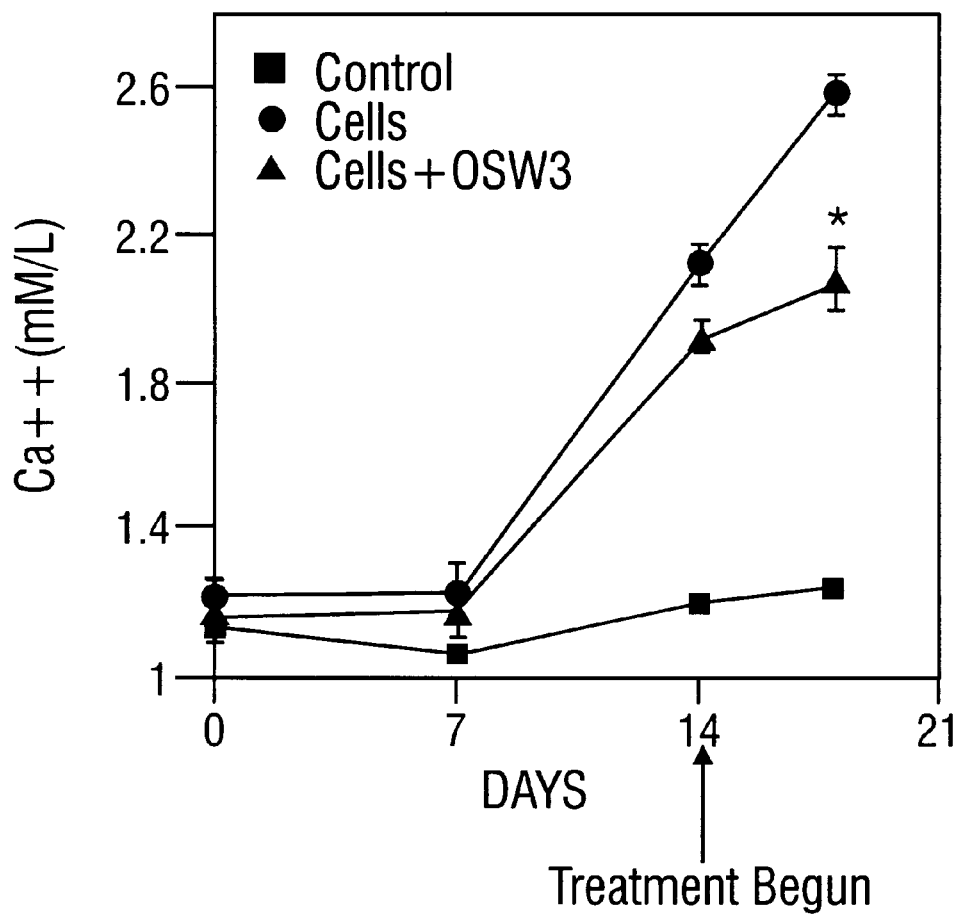
FIG. 7 shows the effect of OSW3 in lowering whole blood calcium levels after evidence of hypercalcemia in nude mice.
Figure 8A:
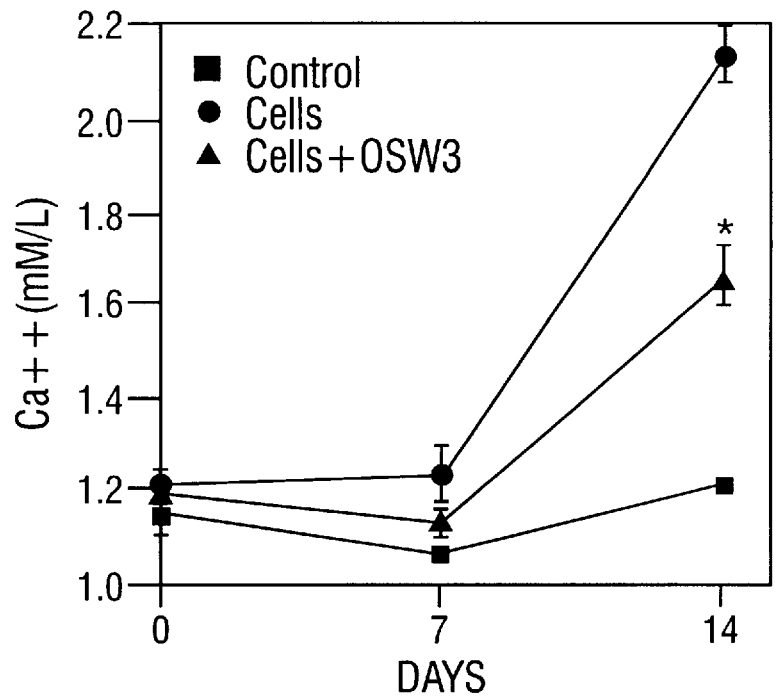
FIG. 8A and FIG. 8B show the effect of OSW3 in reducing whole blood calcium levels prior to onset of hypercalcemia in nude mice.
Figure 8B:
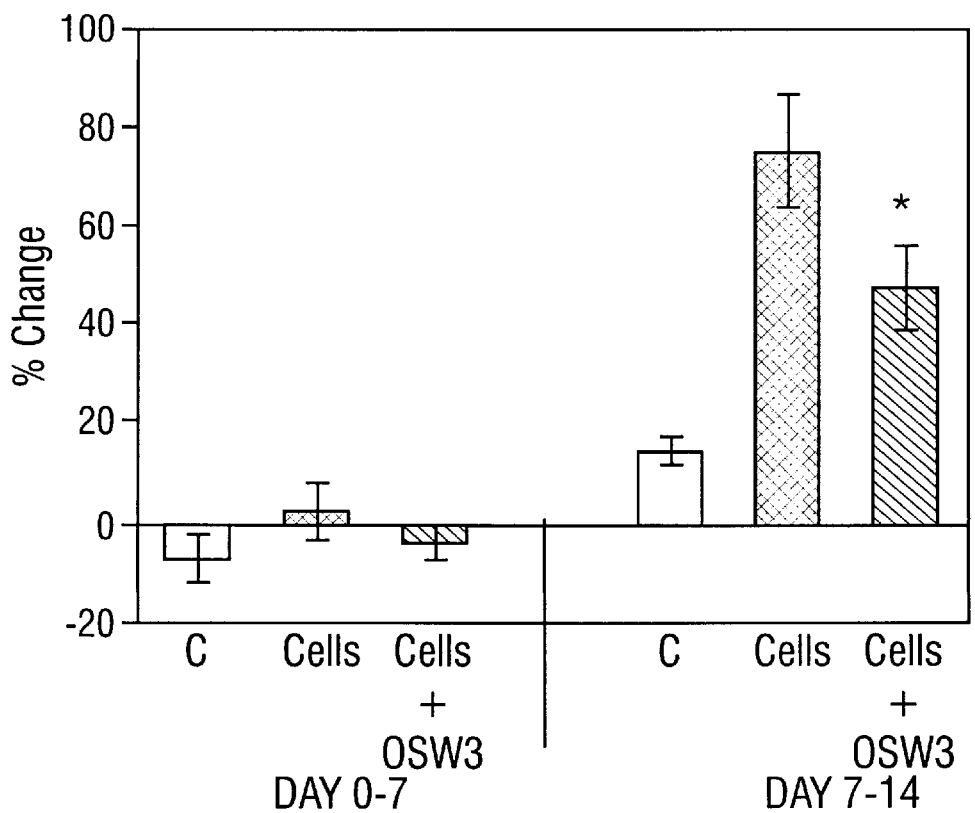
Figure 9:
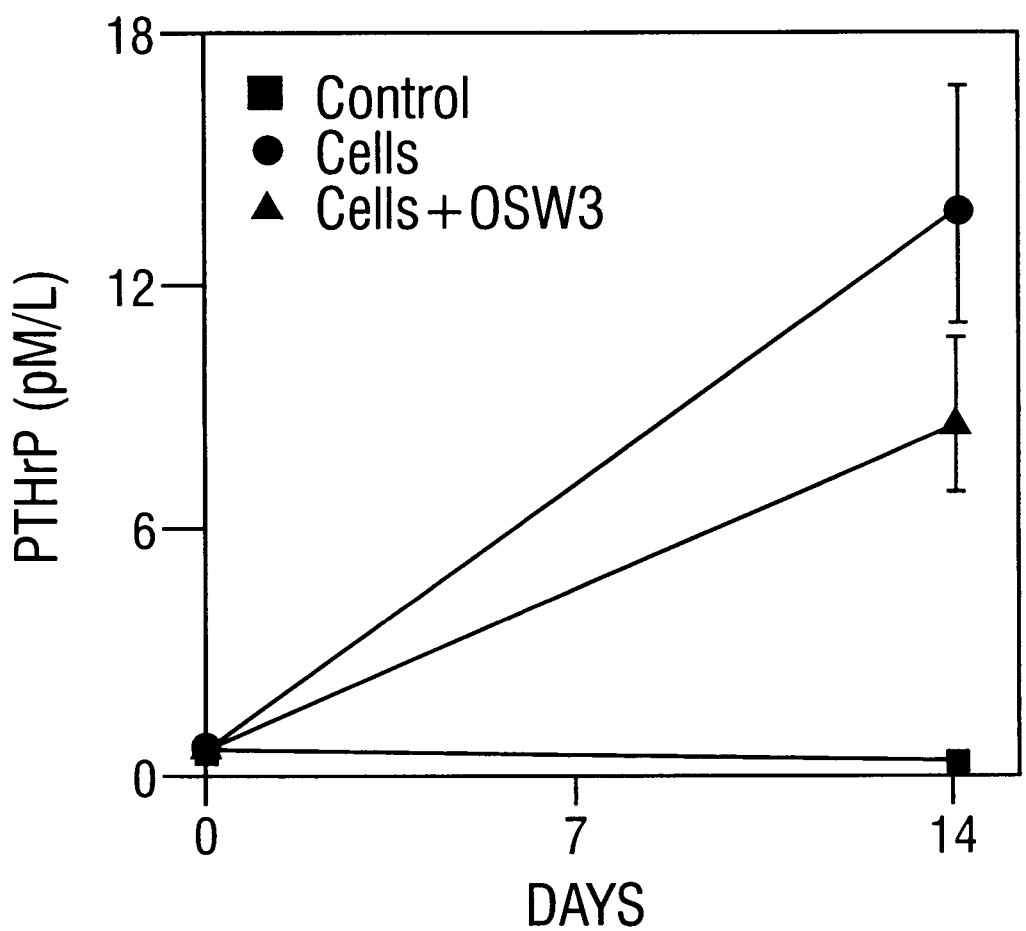
FIG. 9 shows the effect of OSW3 in reducing serum PTH-rP levels prior to onset of hypercalcemia in nude mice.

For all experiments compound is administered when hypercalcemia is evident (treatment phase) or from the time of inoculation of RWGT2 cells (prevention phase). OSW3 (FIG. 1) at 50 mg/kg/day is able to lower whole blood calcium concentrations (FIG. 7) after hypercalcemia is evident when compared to mice injected with vehicle alone. In addition, OSW3 at 50 mg/kg/day is able to lower whole blood calcium concentrations (FIGS. 8A and 8B) and PTH-rP concentrations (FIG. 9) when administered from day 0 when compared to mice injected with vehicle alone.

Figure 10A:
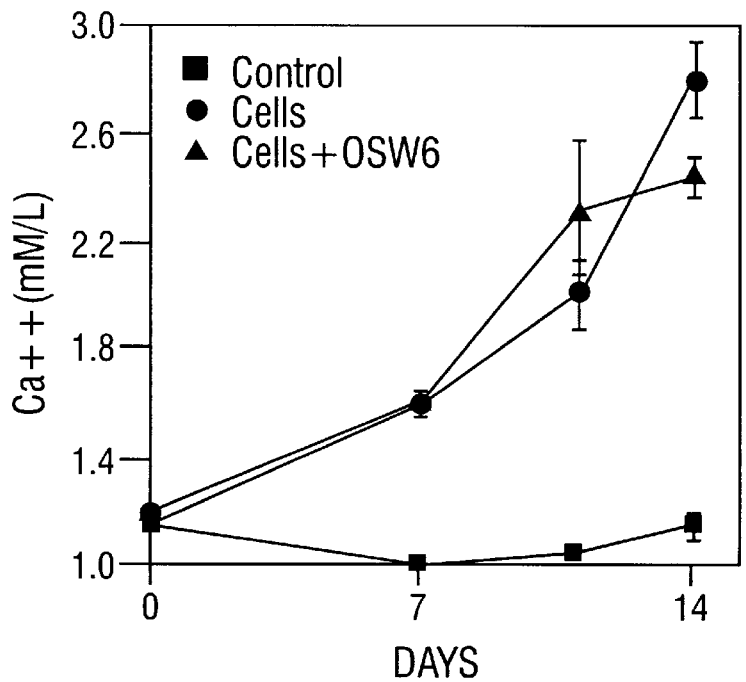
FIG. 10A and FIG. 10B show the effect of OSW6 in lowering whole blood calcium levels after evidence of hypercalcemia in nude mice.
Figure 10B:
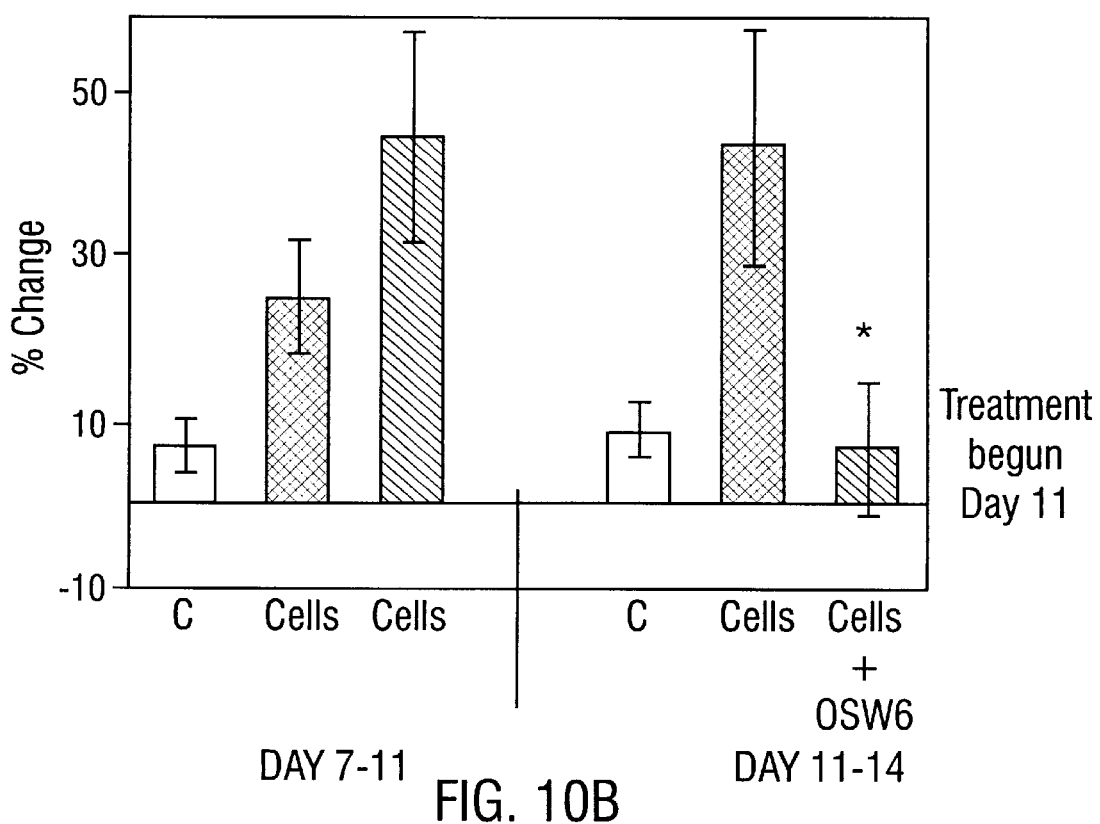
Figure 11:
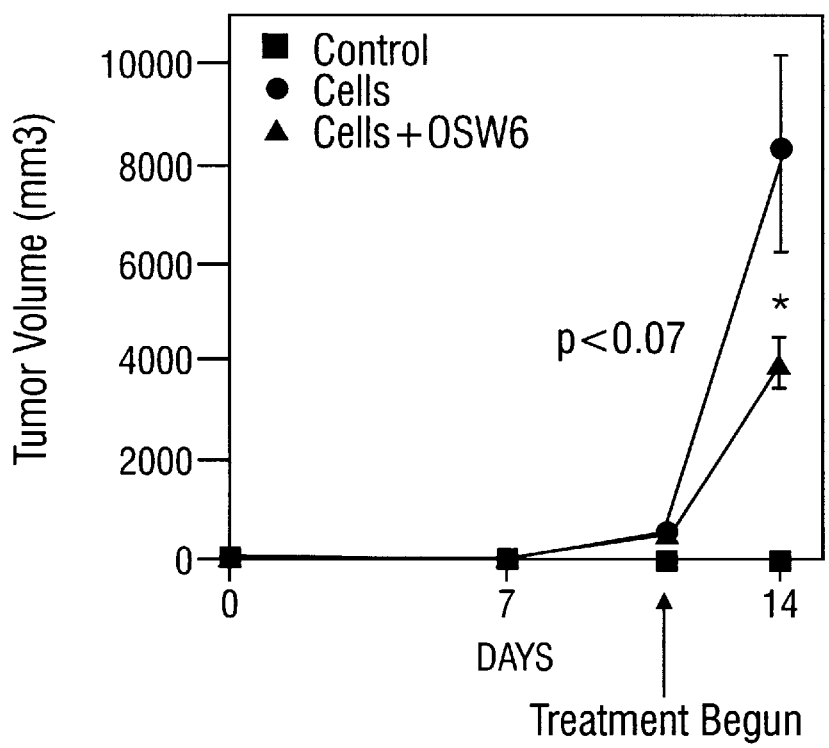
FIG. 11 shows the effect of OSW6 in reducing tumor volume after evidence of hypercalcemia in nude mice.
Figure 12:
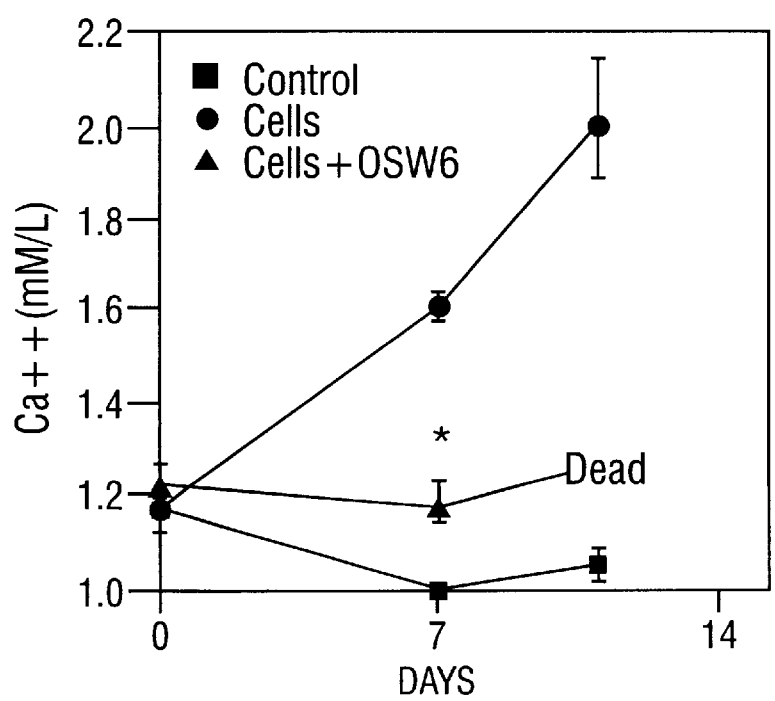
FIG. 12 shows the effect of OSW6 in lowering whole blood calcium levels prior to onset of hypercalcemia in nude mice.

OSW6 (FIG. 5) at 10 mg/kg/day is able to lower whole blood calcium concentrations (FIGS. 10A and 10B) after hypercalcemia is evident when compared to mice injected with vehicle alone. The percent change in whole blood calcium levels when compared to mice injected with vehicle alone is significant (FIGS. 10A and 10B). The size of the tumor is also reduced when hypercalcemic mice are treated with OSW6 (FIG. 11). In addition OSW6 at 10 mg/kg/day is able to significantly lower whole blood calcium concentrations when administered from day 0 when compared to mice injected with vehicle alone (FIG. 12).

Example 4
Analysis of the Ability of Compounds to Inhibit Expression of PTH-rP In Vivo. Bone Metastases Studies.

Compounds which are identified as regulating PTH-rP production were initially tested for their capacity to inhibit bone metastases in vivo by injecting tumor cells into nude mice and treating the mice with the potential inhibitory compounds. Specifically, compounds to be tested were injected into the subcutaneous tissue, intramuscularly, or intravenously into nude mice which were also inoculated with the human cancer cells which produce PTH-rP. The effects on the capacity of the tumor cells to cause osteolytic bone lesions are then assessed over 2–4 weeks.

To demonstrate that compounds inhibit osteolytic bone metastases in vivo, a human tumor cell which is known to express PTH-rP was used. The tumor, named MDA-MB-231, is a human breast cell carcinoma.

The MDA-MB-231 cells are grown in culture in T75 flasks in D-minimal essential medium (DMEM, Hazelton Biologics Inc., Lenexa, Kans.) with 10% fetal calf serum and passaged twice a week. To prepare for mouse inoculation, cells were trypsinized, washed twice with phosphate buffered saline (PBS) and resuspended in PBS to a final concentration of $10^5$ cells/100 μl. The suspended cells are then inoculated into the left ventricle of the heart.

All animal studies are conducted in accordance with the NIH Guide for the Care and Use of Laboratory Animals. Female BALB/c nude mice (Harlen), 4–6 weeks of age, are housed in a laminar flow isolator hood with a 12-hour-light/12-hour-dark cycle. Water, supplemented with multivitamins (Lymphomed, Melrose Park, Ill.) and autoclaved mouse chow (Ralston-Purina, St. Louis, Mo.) were provided ad libitum.

Weekly, the mice are weighed and whole blood samples for ionized calcium ($Ca^{2+}$) determination are obtained by retro-orbital puncture under anesthesia and measured using a Ciba Corning 634 ISE $Ca^{++}$/pH analyzer.

The number of osteolytic bone metastases is determined on radiographs as described by Nakai (1992). Weekly, animals are anesthetized deeply, laid down in a prone position against the film (22×27 cm X-O Mat AR, Kodak, Rochester, N.Y.) and exposed with an x-ray at 35 KVP for 6 seconds using a Faxitron Radiographic Inspection Unit (Model 8050-020, Field Emission Corporation, Inc.). Films are developed using a RP X-O Mat processor (Model M6B, Kodak). The area of osteolytic bone metastases is calculated using a computerized image analysis system in which examination of osteolytic lesions from radiographs is achieved using a fluorescent light box (Kaiser, Germany) and Macro TV Zoom lens 18–108 mm f2,5 (Olympus, Japan) attached to a color video camera (Model DXC-1 51 Sony, Japan). Video images are captured using a frame grabber board (Targa+, Truevision, Inc., USA) with an IBM compatible 486/33 Mhz computer system. Quantitation of lesion area is performed using image analysis software (Java, Jandel Video Analysis, Jandel Scientific, Calif.).

Figure 13A:
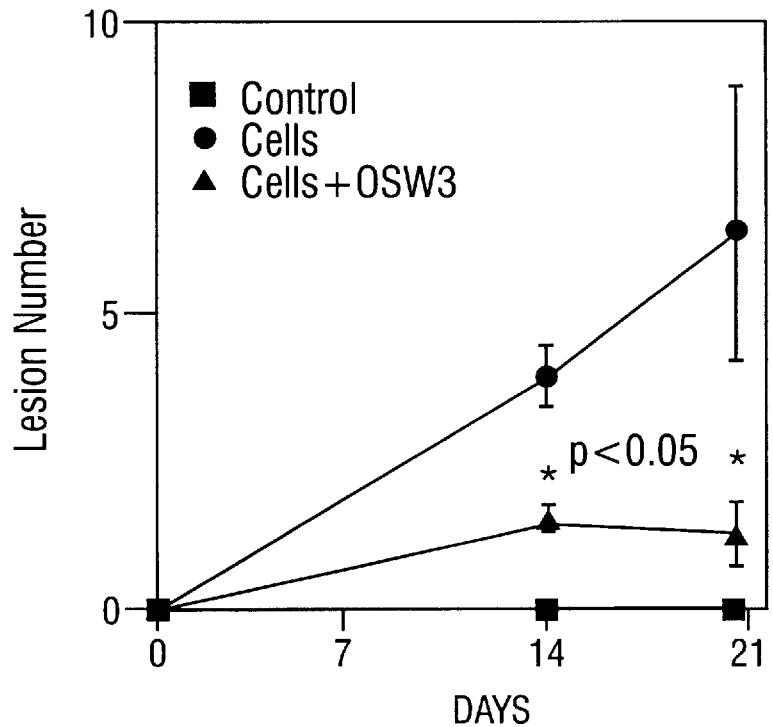
FIG. 13A and FIG. 13B show the effect of OSW3 in reducing lesion number and lesion volume prior to onset of bone metastasis in nude mice.
Figure 13B:
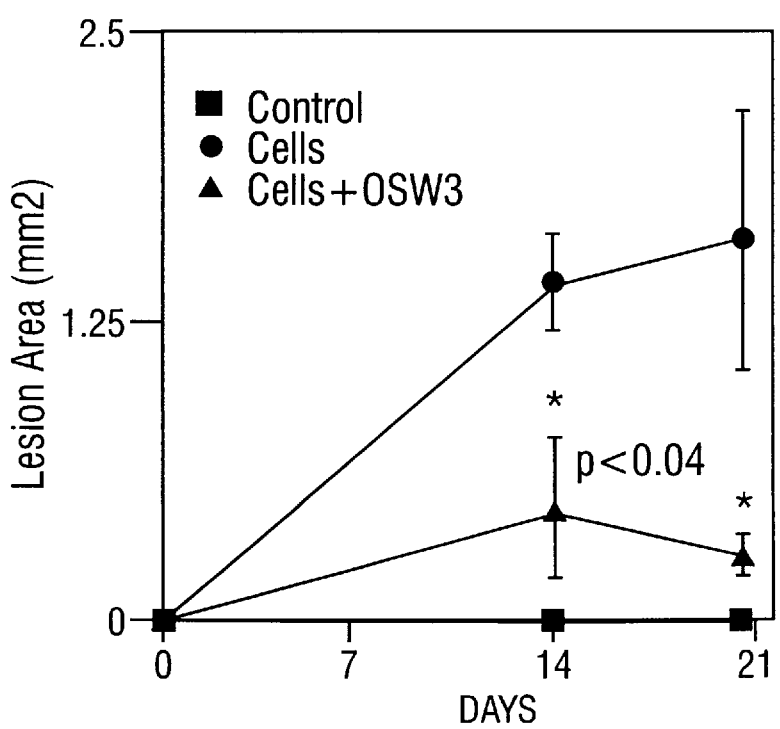

For all experiments compound is administered when osteolytic bone metastases is evident (treatment phase) or from the time of inoculation of MDA-MB-231 cells (prevention phase). OSW3 (FIG. 1) at 50 mg/kg/day is able to significantly lower both lesion number and lesion area of osteolytic metastases due to MDA-MB-231 cells when compared with mice injected with vehicle alone (FIGS. 13A and 13B).

Figure 14A:
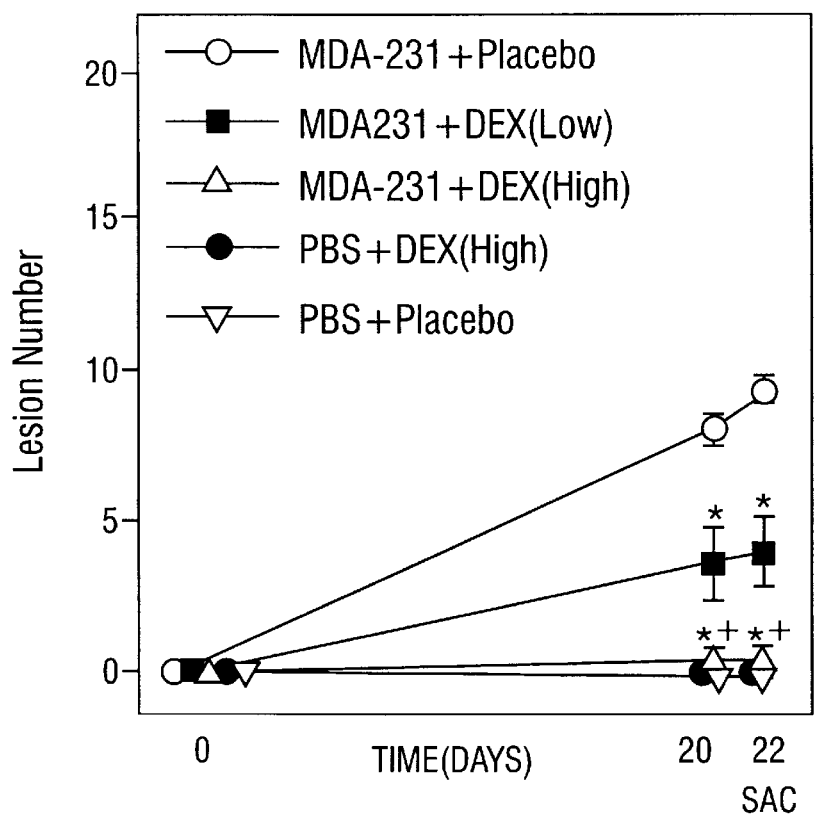
FIG. 14A and FIG. 14B show the effect of dexamethasone in reducing lesion number and lesion volume prior to onset of bone metastasis in nude mice.
Figure 14B:
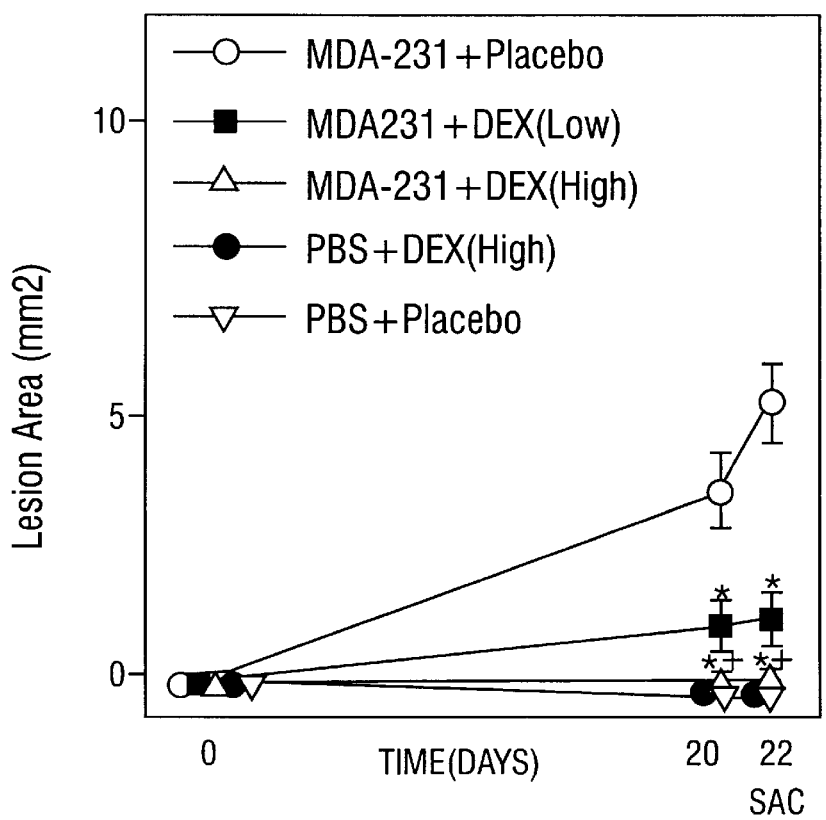

Dexamethasone (FIG. 4) at 1 mg/kg/day (low dose) or 2.6 mg/kg/day (high dose) is able to significantly lower both lesion number and lesion area of osteolytic metastases due to MDA-MB-231 cells when compared with mice injected with vehicle alone (FIGS. 14A and 14B).

Example 5
Analysis of the Ability of Compounds to Stimulate Expression of PTH-rP In Vitro Regulation of expression of PTH-rP was assessed by culturing breast cancer cells with and without compounds which might regulate PTH-rP expression. The luciferase activity was assessed by luminometer. Cell lysates were prepared and the luciferase enzyme assay was carried out using assay protocols and the assay kit from Promega (Madison, Wis.). Routinely, 20 μl of cell lysate was mixed with 100 μl of luciferase assay reagent (270 μM coenzyme A, 470 μM luciferin and 530 μM ATP) and the luciferase activity was measured for 10 seconds in a Turner TD-20e luminometer. The values were normalized with respect to the protein concentration obtained from each experimental sample. The protein concentration was assessed using Bio Rad reagents.

To demonstrate that the present invention is useful in evaluating chemical compounds and agents which regulate PTH-rP production, a random array of chemical compounds obtained commercially from a library of 5000 compounds, purchased from MicroSource Inc., (New Haven, Conn.) was screened. Approximately 1 in 2000 such compounds increased production of PYH-rP in the present assay system compared with the positive control. These compounds were shown to be non-toxic for the tumor cells. Such compounds identified from the random library were subjected to detailed dose-response curves to demonstrate that they stimulate PTH-rP messenger RNA expression, and that they increase other effects associated with PTH-rP in vitro.

Figure 6:
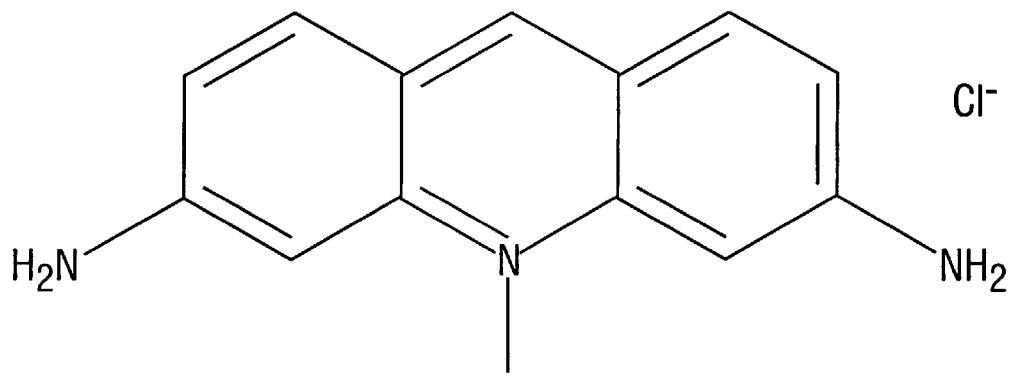
FIG. 6 shows the compound acriflavinium hydrochloride, known as OSWs1.
Figure 15A:
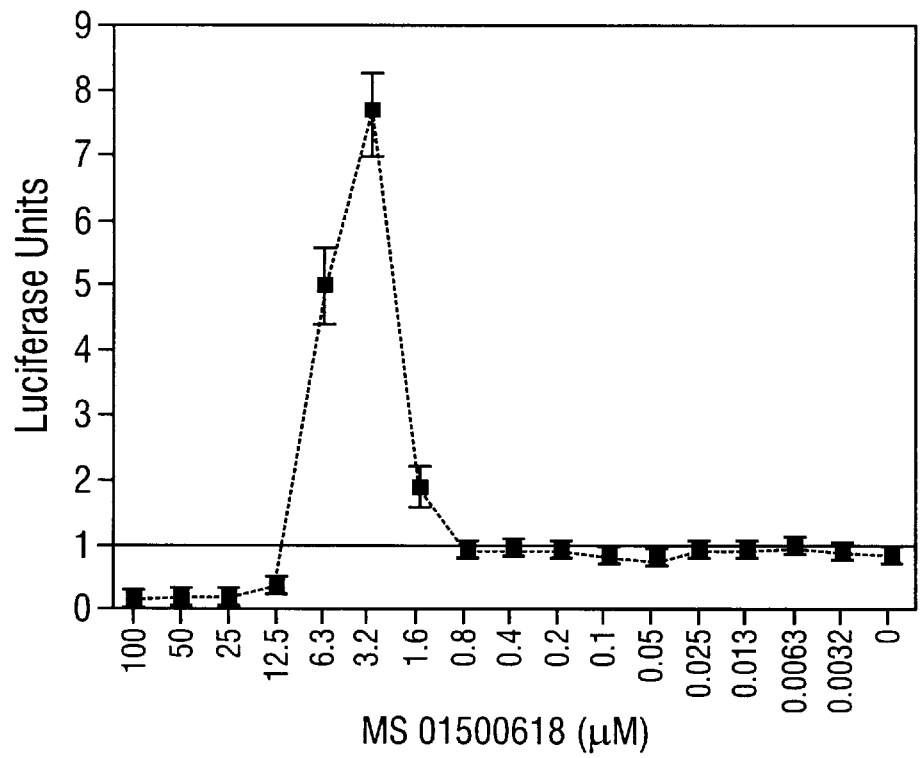
FIG. 15A and FIG. 15B shows the effect of OSWs1 in stimulating the PTH-rP promoter in vitro.
Figure 15B:
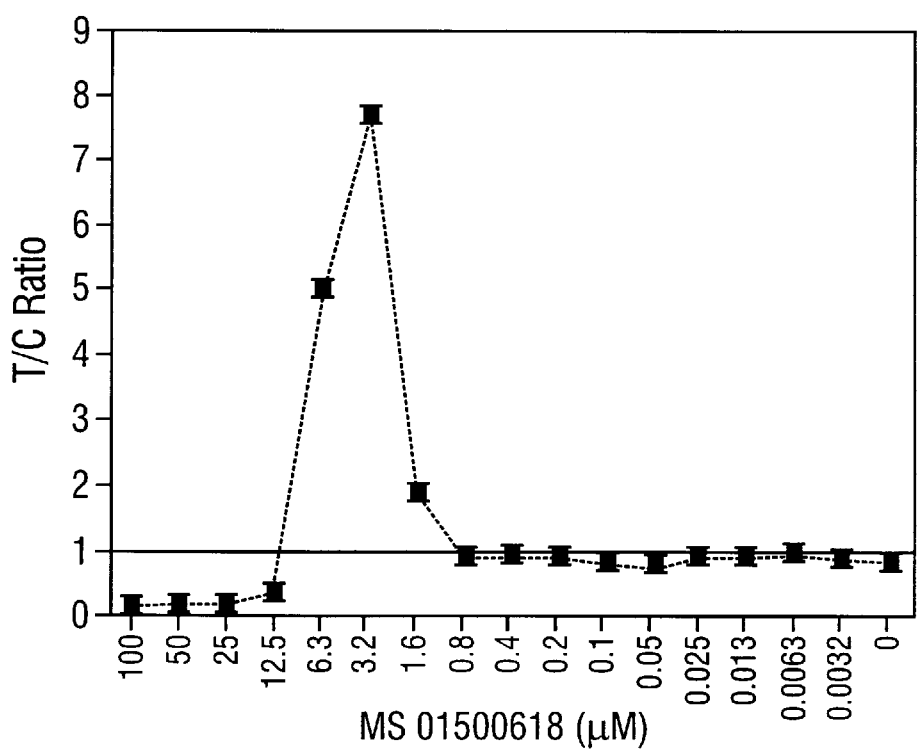

The compound designated MS 01500618 was able to stimulate the present assay about 8 fold at a concentration of 3.2 μM (FIGS. 15A and 15B). This compound is acriflavinium hydrochloride, known as OSWs1 (FIG. 6).

REFERENCES

The following references, to the extent that they provide exemplary procedural or other details supplementary to those set forth herein, are specifically incorporated herein by reference.

Bouizar Z, Spyratos F, Deytieux S, de Vernejoul MC, Jullienne A. Polymerase chain reaction analysis of parathyroid hormone-related protein. Cancer Res 53:5076–5078, 1993

Bundred NJ, Walker RA, Ratcliffe WA, Warwick J, Morrison JM, Ratcliffe JG. Parathyroid hormone related protein and skeletal morbidity in breast cancer. Eur J Cancer 28:690–692, 1992.

Burtis WJ, Wu T, Bunch C, Wysolmerski JJ, Insogna KL, Weir EC, Broadus AE, Stewart AF. Identification of a novel 17,000 dalton parathyroid hormone-like adenylate cyclase-stimulating protein from a tumor associated with humoral hypercalcemia of malignancy. J Biol Chem 262:7151–7156, 1987.

Current Protocols in Molecular Biology. Ed. F. M. Ausubel, et al., pp. 9.1.3–9.1.4, 1996.

Guise TA, Yoneda T, Yates AJ, Mundy GR. The combined effect of tumor-produced parathyroid hormone-related protein and transforming growth factor α enhance hypercalcemia in vivo and bone resorption. J Clin Endocrinol. Metab. 77:40–45, 1993.

Li X, Drucker DJ. Parathyroid hormone-related peptide is a downstream target for ras and src activation. J Biol Chem 269:6263–6266, 1994.

Liapis H, Crouch EC, Grosso LE, Kitazawa S, Wick MR. Expression of parathyroid-like protein in normal, proliferative, and neoplastic human breast tissues. Am J Pathol 143:1169–1178, 1993.

Moseley JM, Kubota M, Diefenbach-Jagger H, Wettenhall REH, Kemp BE, Suva LJ, Rodda CP, Ebeling PR, Hudson PJ, Zajac JD, Martin TJ. Parathyroid hormone-related protein purified from a human lung cancer cell line. Proc Natl Acad Sci 84:5048–5052, 1987.

Mundy GR. Malignancy and hypercalcemia. IN Calcium Homeostasis—Hypercalcemia and Hypocalcemia. Second Editor, Martin Dunitz, London, 1990.

Powell GJ, Southby J, Danks JA, Stillwell RG, Hayman JA, Henderson MA, Bennett RC, Martin TJ. Localization of parathyroid hormone-related protein in breast cancer metastases— increased incidence in bone compared with other sites. Cancer Res 51:3059–3061, 1991.

Southby J, Kissin MW, Danks JA, Hayman JA, Moseley JM, Henderson MA, Bennett RC, Martin TJ. Immunohistochemical localization of parathyroid hormone-related protein in human breast cancer. Cancer Res 50:7710–7716, 1990.

Strewler GJ, Stem PH, Jacobs JW, Eveloff J, Klein RF, Leung SC, Rosenblatt M, Nissenson RA. Parathyroid hormone-like protein from human renal carcinoma cells: structural and functional homology with parathyroid hormone, J Clin Invest 80:1803–1807, 1987.

Vargas SJ, Gillespie MT, Powell GJ, Southby J, Danks JA, Moseley JM, Martin TJ. Localization of parathyroid hormone-related protein mRNA expression in breast cancer and metastatic lesions by in situ hybridization. J Bone Min Res 7:971–979, 1992.

Wysolmerski JJ, Vasavada R, Foley J, Weir EC, Burtis WJ, Kukreja SC, Guise TA, Broadus AE, Phillbrick WM. Transactivation of the PTH-rP gene in squamous carcinomas predicts the occurrence of hypercalcemia in athymic mice. Cancer Res 56:1043–104, 1996.

Yin JJ, Taylor SD, Yoneda T, Dallas M, Boyce BF, Kumagai Y, Mundy GR, Guise TA. Evidence that parathyroid hormone-related protein (PTH-rP) causes osteolytic metastases without hypercalcemia. J Bone Min Res 10 (Suppl 1) #122, 1995.

Nakai M, Mundy GR, Williams PJ, Boyce B, Yoneda T. A synthetic antagonist to laminin inhibits the formation of osteolytic metastases by human melanoma cells in nude mice. Cancer Res 52:5395–5399, 1992.

Guise TA, Yoneda T, Yates AJ, Mundy GR. The combined effect of tumor-produced parathyroid hormone-related protein and transforming growth factor alpha enhance hypercalcemia in vivo and bone resorption in vitro. J Clin Endocrinol Metab 77:40–45, 1993.

Suda N, Gillespie MT, Traianedes K, Zhou H, Ho PWM, Hards DK, Allan EH, Martin TJ, Moseley JM. Expression of parathyroid hormone-related protein in cells of osteoblast lineage. J Cell Physiology 166:96–104, 1996.

Stewart AF. PTHrP(1-36) as a skeletal anabolic agent for the treatment of osteoporosis. Bone 19:303–306, 1996.

Vickery BH, Avnur Z, Cheng Y, Chiou SS, Leaffer D, Caufield JP, Kimmel DB, Ho T, Krstenansky JL. RS-66271, a c-terminally substituted analog of human parathyroid hormone-related protein (1–34), increases trabecular and cortical bone in ovariectomized, osteopenic rats. J Bone Min Res 11:1943–1951, 1996.

Karaplis AC, Luz A, Glowacki J, Bronson RT, Tybulewicz VL, Kronenberg HM, Mulligan RC. Lethal skeletal dysplasia from targeted disruption of the parathyroid hormone-related peptide gene. Genes Dev 8:277–289, 1994.

Lanske B, Karaplis AC, Lee K, Luz A, Vortkamp A, Pirro A, Karperien M, Defize LHK, Ho C, Mulligan RC, Abou-Samra A, Juppner H, Segre GV, Kronenberg HM. PTH/PTHrP receptor in early development and indian hedgehog-regulated bone growth. Science 273:663–666, 1996.

Vortkamp A, Lee K, Lanske B, Segre GV, Kronenberg HM, Tabin CJ. Regulation of rate of cartilage diferentiation by indian hedgehog and pth-related protein. Science 273:613–622, 1996.

---

What is claimed is:

1. A method for screening a compound for inhibition of PTH-rP production in mammalian cells comprising the steps of:

(i) providing an expression construct comprising a PTH-rP promoter and a reporter gene, wherein said reporter gene is under transcriptional control of said promoter;

(ii) transfecting said mammalian cells with said expression construct;

(iii) contacting said transfected cell with said compound; and (iv) identifying a non-toxic compound that reduces expression of said reporter gene from said promoter.

2. The method of claim 1, wherein said compound inhibits PTH-rP production in mammalian cells.

3. The method of claim 1, wherein said reporter gene is selected from the group consisting of firefly luciferase, chloramphenicol acetyl transferase, β-galactosidase, green fluorescent protein, human growth hormone, alkaline phosphatase and β-glucuronidase.

4. The method of claim 3, wherein said reporter gene is firefly luciferase.

5. The method of claim 1, wherein said promoter for PTH-rP is cloned from genomic DNA.

6. The method of claim 5, wherein said promoter has the sequence of SEQ ID NO:1.

7. The method of claim 1, wherein said expression construct is the plasmid pGL3B-PTH-rP 1.1.

8. The method of claim 1, wherein said mammalian cells are human cells.

9. The method of claim 8, wherein said human cells are tumor cells.

10. The method of claim 9, wherein said tumor cells are breast cancer cells.

11. The method of claim 10, wherein said breast cancer cells are MDA-MB-231 cells.

12. The method of claim 9, wherein said tumor cells are lung cancer cells.

13. The method of claim 12, wherein said lung cancer cells are RWGT2 cells.

14. The method of claim 8, wherein said human cells are bone cells.

15. The method of claim 14, wherein said bone cells are selected from the group consisting of MC3T3-E1, MG-63, U2OS, UMR-106, ROS17/2.8 and SAOS-2.

16. A method for screening a compound for stimulation of PTH-rP production in mammalian cells comprising the steps of:

(i) providing an expression construct comprising a PTH-rP promoter and a reporter gene, wherein said reporter gene is under transcriptional control of said promoter;

(ii) transfecting said mammalian cells with said expression construct;

(iii) contacting said transfected cell with said compound; and (iv) identifying a non-toxic compound that increases expression of said reporter gene from said promoter.

17. The method of claim 16, wherein said compound stimulates PTH-rP production in mammalian cells.

* * * * *